US008431162B2

(12) United States Patent
Zuba-Surma et al.

(10) Patent No.: US 8,431,162 B2
(45) Date of Patent: Apr. 30, 2013

(54) SUBPOPULATIONS OF BONE MARROW-DERIVED ADHERENT STEM CELLS AND METHODS OF USE THEREFOR

(75) Inventors: Ewa K. Zuba-Surma, Louisville, KY (US); Buddhadeb Dawn, Louisville, KY (US); Ahmed Abdel-Latif, Lexington, KY (US); Roberto Bolli, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 901 days.

(21) Appl. No.: 12/261,344

(22) Filed: Oct. 30, 2008

(65) Prior Publication Data

US 2009/0110668 A1 Apr. 30, 2009

Related U.S. Application Data

(60) Provisional application No. 61/000,977, filed on Oct. 30, 2007.

(51) Int. Cl.
*A61K 35/28* (2006.01)
*C12N 5/02* (2006.01)
*C12N 5/00* (2006.01)

(52) U.S. Cl.
USPC .......................................... 424/577; 435/372

(58) Field of Classification Search ........................ None
See application file for complete search history.

(56) References Cited

U.S. PATENT DOCUMENTS

| | | | | |
|---|---|---|---|---|
| 5,736,396 | A | 4/1998 | Bruder et al. | |
| 5,750,397 | A | 5/1998 | Tsukamoto et al. | |
| 2008/0206343 | A1 * | 8/2008 | Edinger et al. | 424/489 |
| 2009/0110668 | A1 | 4/2009 | Zuba-Surma et al. | |
| 2011/0189136 | A1 * | 8/2011 | Ratajczak et al. | 424/93.7 |

OTHER PUBLICATIONS

Abdel-Latif et al. (2007). Adult bone marrow-derived cells for cardiac repair: a systematic review and meta-analysis. *Archives of Internal Medicine, American Medical Association*. 167(10):989-997.
Boxall and Jones (2012). Markers for characterization of bone marrow multipotential stromal cells. *Stem Cells Intl*. 2012:1-12.
Duff et al. (2003). CD105 is important for angiogenesis: Evidence and potential applications. *FASEB J.* 17(9):984-992.
Gekas et al. (2005). The placenta is a niche for hematopoietic stem cells. *Devel Cell*. 8:365-375.
Guo et al. (1998). Demonstration of an early and a late phase of ischemic preconditioning in mice. *Am J Physiol*. 275:H1375-1387.
Kinnaird et al. (2004). Bone-marrow-derived cells for enhancing collateral development: mechanisms, animal data, and initial clinical experiences. *Circ Res*. 95:354-363.
Kucia et al. (2008). Identification of very small embryonic like (VSEL) stem cells in bone marrow. *Cell Tissue Res*. 331:125-134.
Li et al. (2005). Mesenchymal stem cells derived from human placenta suppress allogeneic umbilical cord blood lymphocyte proliferation. *Cell Res* 15:539-547. [Abstract Only].
Mangi et al. (2003). Mesenchymal stem cells modified with Akt prevent remodeling and restore performance of infarcted hearts. *Nat Med*. 9:1195-1201.
Miao et al. (2006). Isolation of mesenchymal stem cells from human placenta: Comparison with human bone marrow mesenchymal stem cells. *Cell Biol Intl*. 2006:681-687.
Nagaya et al. (2005). Transplantation of mesenchymal stem cells improves cardiac function in a rat model of dilated cardiomyopathy. *Circulation*. 112:1128-1135.
Nimgaonkar et al. (1995) A unique population of CD34+ cells in cord blood. *Stem Cells*. 13:158-166. [Abstract Only].
Notification of Transmittal of the International Search Report and the Written Opinion of the International Searching Authority, or the Declaration corresponding to International Application No. PCT/US2008/081761 dated Oct. 14, 2010.
Pierelli et al. (2001) CD105 (Endoglin) expression on hematopoietic stem/progenitor cells. Leuk *Lymphoma*. 42:1195-206. [Abstract Only].
Pittenger et al. (2004). Mesenchymal stem cells and their potential as cardiac therapeutics. *Circ Res*. 95:9-20.
Rebelatto et al. (2008). Dissimilar differentiation of mesenchymal stem cells from bone marrow, umbilical cord blood, and adipose tissue. *Exp Biol Med*. 233:901-913.
Silva et al. (2003). The profile of gene expression of human marrow mesenchymcal stem cells. *Stem Cells*. 21:661-669.
Wang et al. (2011) Differential hematopoietic supportive potential and gene expression of stroma cell lines from midgestation mouse placenta and adult bone marrow. *Cell Transplant* 20:707-726. [Abstact Only].

* cited by examiner

*Primary Examiner* — Michail Belyavskyi
(74) *Attorney, Agent, or Firm* — Jenkins, Wilson, Taylor & Hunt, P.A.

(57) ABSTRACT

The presently disclosed subject matter provides an isolated subpopulation of bone marrow-derived adherent stem cells that are purified from bone marrow-derived adherent cells. Also provided are methods for isolating the subpopulation of bone marrow-derived adherent stem cells from bone marrow-derived adherent cells and for using the isolated subpopulation of bone marrow-derived adherent stem cells for treating tissue and/or organ damage in a subject.

5 Claims, 22 Drawing Sheets

SUBPOPULATIONS OF BONE MARROW-DERIVED ADHERENT STEM CELLS AND METHODS OF USE THEREFOR

CROSS REFERENCE TO RELATED APPLICATION

The presently disclosed subject matter claims the benefit of U.S. Provisional Patent Application Ser. No. 61/000,977, filed Oct. 30, 2007, the disclosure of which is incorporated herein by reference in its entirety

GOVERNMENT INTEREST

This presently disclosed subject matter was made with U.S. Government support under Grant No. 1 R21 HL089737-01A1 awarded by U.S. National Institutes of Health/National Heart, Lung, and Blood Institute (NHLBI). Thus, the U.S. Government has certain rights in the presently disclosed subject matter.

TECHNICAL FIELD

The presently disclosed subject matter relates, in general, to the identification, isolation, and use of a subpopulation of bone marrow-derived adherent stem cells. More particularly, the presently disclosed subject matter relates to isolating said subpopulation of bone marrow-derived adherent stem cells and employing the same to treat tissue and/or organ damage in a subject in need thereof.

BACKGROUND

The use of stem cells and stem cell derivatives has gained increased interest in medical research, particularly in the area of providing reagents for treating tissue damage that result from genetic defects, injuries, and/or disease processes. Ideally, cells that are capable of differentiating into the affected cell types could be transplanted into a subject in need thereof, where they would interact with the organ microenvironment and supply the necessary cell types to repair the injury.

Stem cells can be harvested from a number of organs, including the bone marrow, adipose tissue, skeletal muscle, and other organs. Considerable effort has been expended to isolate adult stem cells from a number of different tissues for use in regenerative medicine. For example, U.S. Pat. No. 5,750,397 to Tsukamoto et al. discloses the isolation and growth of human hematopoietic stem cells that are reported to be capable of differentiating into lymphoid, erythroid, and myelomonocytic lineages. U.S. Pat. No. 5,736,396 to Bruder et al. discloses methods for lineage-directed differentiation of isolated human mesenchymal stem cells under the influence of appropriate growth and/or differentiation factors. The derived cells can then be introduced into a host for mesenchymal tissue regeneration or repair.

Traditionally, adherent primitive cells (also termed "mesenchymal stem cells") are isolated via adhesion to plastic for 24-72 hours. However, it is well known that the population of cells isolated via adhesion is considerably heterogeneous in terms of phenotype, antigen expression, morphology, biological activities, and differentiation potential. Bone marrow (BM)-derived mesenchymal stem cells (MSCs), for example, can be induced to differentiate into osteogenic, chondrogenic, adipogenic, myogenic, neural, and other nonhematopoietic lineages.

Ischemic heart disease is the single most prevalent cause of death and morbidity in the USA (Heart Disease and Stroke Statistics, 2006). Despite pharmacotherapy, the infarcted left ventricle (LV) undergoes progressive remodeling leading to permanent impairment of cardiac function and development of congestive heart failure (Pfeffer et al., 1979; Pfeffer et al. 1990; McMurray & Pfeffer, 2005). Since no intervention is currently available for restoring the lost myocardial tissue, the treatment of post-myocardial infarction (MI) heart failure remains palliative and the prognosis for patients with large MI remains poor (Braunwald & Bristow, 2000; McMurray & Pfeffer, 2005). Although recent evidence indicates that therapy with BM-derived cells can improve LV function, ameliorate remodeling, and improve perfusion, the benefits have varied tremendously from one study to another and the underlying mechanisms remain highly controversial (Vassilopoulos et al. 2003; Wang et al. 2003; Chien, 2004; Balsam et al. 2004; Murry et al. 2004; Laflamme & Murry, 2005).

This inconsistency has significant consequences on the usefulness of these mixed cell populations for in vivo therapeutic purposes. For example, while clinical trials of MSC therapy for infarct repair are already underway, a critical examination of studies in vitro and cardiac repair in vivo has revealed a profound lack of consistency in major findings, including MSC-induced angiogenesis, myogenesis, anti-apoptotic effects, and a combination thereof, often termed "paracrine effects". The bases for this inconsistency of performance are currently unknown.

Thus, there continues to be a need for new approaches to generate populations of transplantable cells suitable for a variety of applications, including but not limited to treating injury and/or disease of various organs and/or tissues.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for isolating a subpopulation of bone marrow-derived adherent stem cells. In some embodiments, the methods comprise (a) contacting bone marrow-derived adherent stem cells with a plurality of antibodies, wherein each of the plurality of antibodies is specific for an antigen selected from the group consisting of CD45, CD34, Sca-1, c-kit, Thy1/CD90, and CD105 under conditions sufficient to allow binding of each antibody to its target, if present, on each cell of the population of cells; and (b) selecting a subpopulation of cells that are $CD34^+$ or $Sca\text{-}1^+$, and are also $CD45^-$, $c\text{-}kit^-$, $Thy1/CD90^+$, and $CD105^-$. In some embodiments, the contacting step comprises contacting the bone marrow-derived adherent stem cells with a plurality of antibodies simultaneously or iteratively. In some embodiments, the presently disclosed methods further comprise expanding the bone marrow-derived adherent stem cells in culture for about 7 days prior to performing the contacting step.

The presently disclosed subject matter also provides isolated subpopulations of bone marrow-derived adherent stems cells, wherein the isolated subpopulation of bone marrow-derived adherent stem cells comprises $CD34^+/CD45^-/c\text{-}kit^-/$ $Thy1^+/CD105^-$ or $Sca\text{-}1^+/CD45^-/c\text{-}kit^-/Thy1^+/CD105^-$ cells isolated from adherent bone marrow cells.

The presently disclosed subject matter also provides method for treating an injury to a tissue in a subject. In some embodiments, the methods comprise administering to the subject a composition comprising a plurality of isolated $CD34^+/CD45^-/c\text{-}kit^-/Thy1^+/CD105^-$ or $Sca\text{-}1^+/CD45^-/c\text{-}kit^-/Thy1^+/CD105^-$ bone marrow-derived adherent stem cells in a pharmaceutically acceptable carrier, in an amount and via a route sufficient to allow at least a fraction of the bone marrow-derived adherent stem cells to engraft the tissue and differentiate therein, whereby the injury is treated. In some embodiments, the injury is selected from the group consisting of an ischemic injury and a myocardial infarction. In some embodiments, the tissue exhibits an impaired function secondary to one or more causes, identifiable or not, other than ischemic injury.

The presently disclosed methods and compositions can be employed in the treatment of subjects of any species. In some embodiments, the subject is a mammal. In some embodiments, the subject is a human.

It is an object of the presently disclosed subject matter to provide a method for isolating a subpopulation of bone marrow-derived adherent stem cells.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

DETAILED DESCRIPTION

Figure 1:
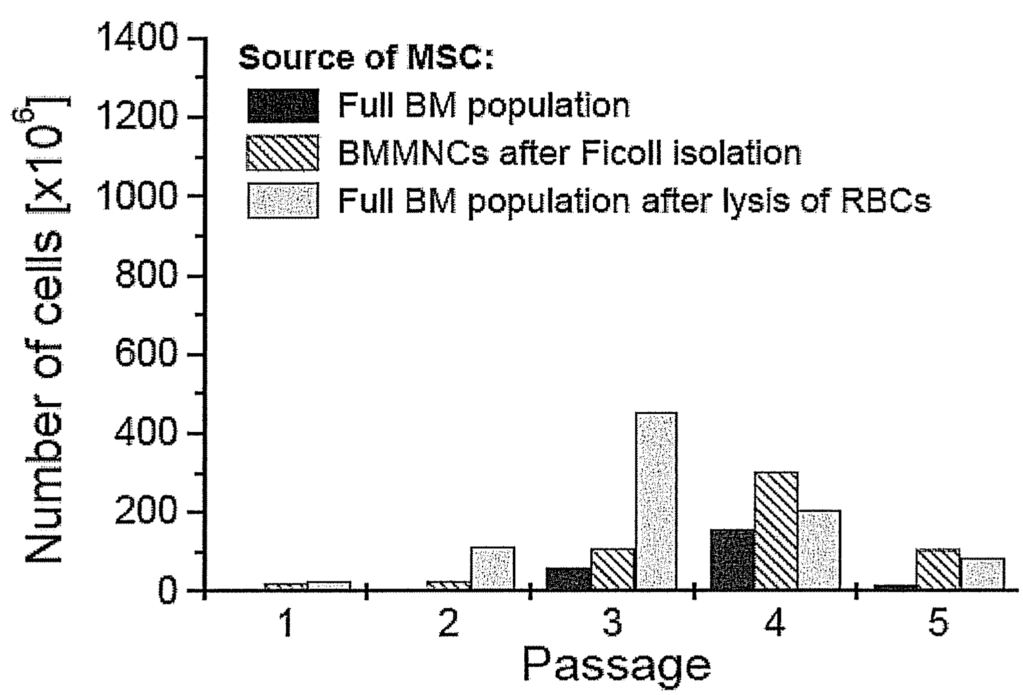
FIG. 1 is a bar graph showing that the expansion capacity of bone marrow-derived adherent mesenchymal stem cells (MSCs) in the same medium (MESENCULT® culture medium) varies depending on the method of isolation before plating, indicating differences between the adherent unfractionated MSC populations.

The present subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Disclosed herein are methods for the isolation of a specific subpopulation of bone marrow-derived adherent mesenchymal stem cells based on surface antigen expression. For this purpose, bone marrow cells were isolated from the femur and tibia of adult mice, and cells were allowed to adhere to plastic culture plates in DMEM-F12 medium. After a sufficient time period (e.g., 3 days), the non-adherent cells were discarded and the remaining cells allowed to expand. Expanded cells were detached by trypsin, stained with fluorochrome-conjugated primary antibodies against various surface markers (Sca-1, CD45, c-kit, Thy1, CD105, and CD11b) and analyzed by fluorescence activated cell sorting (FACS). Stem cells with the $Sca\text{-}1^+/CD45^-/c\text{-}kit^-/Thy1^+/CD105^-$ phenotype were sorted and collected in 1 ml of DMEM-F12 in snap-cap tubes.

These cells were transferred to a cell culture incubator shortly after sorting and cultured in appropriate media to induce cardiomyogenic and endothelial differentiation.

During culture as well as at the end of culture, differentiation of these specific MSCs into cardiac cells and endothelial cells was examined by morphology and quantitation of protein expression. The differentiation of these MSCs was confirmed by the detection of cardiac-specific proteins in the differentiated cells using specific staining for these proteins. Their differentiation was also confirmed by detecting nuclear proteins that have been proven to be specifically present in cardiac cells. Differentiation into an endothelial phenotype was confirmed by quantitatively examining the formation of endotubules in MATRIGEL™ matrix as well as by examining the expression of endothelial cell-specific proteins. The Sca-1$^+$/CD45$^-$/c-kit$^-$/Thy1$^+$/CD105$^-$ subpopulation yielded greater numbers of cardiac and endothelial cells compared with other phenotypes. Therefore, this subpopulation represents a good candidate to improve the efficiency of stem cell-mediated cardiac repair when transplanted in patients with heart attacks or heart failure.

I. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms “a”, “an”, and “the” mean “one or more” when used in this application, including the claims, unless the context clearly indicates otherwise. Thus, the phrase “a stem cell” refers to one or more stem cells.

The terms “target tissue” and “target organ” as used herein refer to an intended site for accumulation of one or more cells present in the presently disclosed stem cell subpopulations following administration to a subject. For example, in some embodiments the methods of the presently disclosed subject matter involve a target tissue or a target organ that has been damaged, for example by ischemia or other injury.

The term “control tissue” as used herein refers to a site suspected to substantially lack accumulation of an administered cell. For example, in accordance with the methods of the presently disclosed subject matter, a tissue or organ that has not been injured or damaged is a representative control tissue, as is a tissue or organ other than the intended target tissue. For example, if the injury to be treated is a myocardial infarction, the intended target tissue would be the heart, and essentially all other tissues and organs in the subject can be considered control tissues.

The terms “targeting” and “homing”, as used herein to describe the in vivo activity of a cell (for example, a cell present within the presently disclosed stem cell subpopulations) following administration to a subject, and refer to the preferential movement and/or accumulation of the cell in a target tissue as compared to a control tissue.

The terms “selective targeting” and “selective homing” as used herein refer to a preferential localization of a cell (for example, a cell present within the presently disclosed stem cell subpopulations) that results in an accumulation of one or more members of the administered subpopulation in a target tissue that is in some embodiments about 2-fold greater than accumulation of members of the administered subpopulation in a control tissue, in some embodiments accumulation of one or more members of the administered subpopulation in a target tissue that is in some embodiments about that is about 5-fold or greater, and in some embodiments an accumulation of one or more members of the administered subpopulation in a target tissue that is in some embodiments about that is about 10-fold or greater than in an control tissue. The terms “selective targeting” and “selective homing” also refer to accumulation of one or more members of the administered subpopulation in a target tissue concomitant with an absence of accumulation in a control tissue, in some embodiments the absence of accumulation in all control tissues.

The term “absence of targeting” is used herein to describe substantially no binding or accumulation of one or more members of the administered subpopulation in one or more control tissues under conditions wherein accumulation would be detectable if present. The phrase also is intended to include minimal, background accumulation of one or more members of the administered subpopulation in one or more control tissues under such conditions.

The term “subject” as used herein refers to a member of any invertebrate or vertebrate species. Accordingly, the term “subject” is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein.

Similarly, all genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences by GENBANK® Accession No., are intended to encompass homologous and/or orthologous genes and gene products from other animals including, but not limited to other mammals, fish, amphibians, reptiles, and birds.

The methods of the presently disclosed subject matter are particularly useful for warm-blooded vertebrates. Thus, the presently disclosed subject matter concerns mammals and birds. More particularly contemplated is the isolation, manipulation, and use of subpopulations of BM-derived adherent stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of subpopulations of BM-derived adherent stem cells from livestock, including but not limited to domesticated swine (pigs and hogs), ruminants, horses, poultry, and the like.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods.

The term "isolated", as used in the context of a cell (including, for example, a bone marrow-derived adherent stem cell), indicates that the cell exists apart from its native environment. An isolated cell can also exist in a purified form or can exist in a non-native environment.

As used herein, the term "injury" is to be interpreted broadly to include any impact on a cell, tissue, or organ that results in an undesirable consequence to the cell, tissue, or organ. In some embodiments, an injury results from an insult that is observable or otherwise definable, but the ability to identify the source of the injury is not limiting. Thus, in some embodiments an injury comprises an ischemic injury.

However, in some embodiments injury can include injuries subsequent to which a cell, tissue, and/or organ exhibits an impaired function that is secondary to one or more causes, identifiable or not, other than ischemic injury.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

As used herein, the phrases "subpopulation of bone marrow-derived adherent stem cells", "Sca-1$^+$/CD45$^-$/ckit$^-$/CD90$^+$/CD105$^-$ MSCs", CD34$^+$/CD45$^-$/ckit$^-$/CD90$^+$/CD105$^-$ MSCs", "Sca-1$^+$/CD45$^-$/ckit$^-$/CD90$^+$/CD105$^-$ cells (BMMSC)", and "Sca-1$^+$/CD45$^-$/c-kit$^-$/Thy1$^+$/CD105$^-$ subpopulation" are used interchangeably and refer to a subpopulation of bone marrow cells that are isolated from a mixed population of bone marrow-derived adherent stem cells by the methods disclosed herein. In some embodiments, the subpopulation of bone marrow-derived adherent stem cells is isolated by isolating from a mixed population of bone marrow-derived adherent stem cells a subpopulation of said cells that are Sca-1$^+$ or CD34$^+$ as well as CD45$^-$/c-kit$^-$/Thy1$^+$/CD105$^-$, depending on the source of the bone marrow-derived adherent stem cells. For example, if the source of the bone marrow-derived adherent stem cells is a mouse, the subpopulation of said cells can include those cells that are Sac-1$^+$/CD45$^-$/c-kit$^-$/Thy1$^+$/CD105$^-$. If the source of the bone marrow-derived adherent stem cells is a human, the subpopulation of said cells can include those cells that are CD34$^+$/CD45$^-$/c-kit$^-$/Thy1$^+$/CD105$^-$.

II. Isolation of Subpopulations of Bm-Derived Adherent Stem Cells

MSCs were originally isolated by their adherence to plastic (Friedenstein et al. 1968; Friedenstein et al., 1970; Friedenstein et al., 1976), and this method of MSC isolation continues to be followed in numerous laboratories working on MSC biology. Although more than 20 different surface antigens have been used to characterize adherent MSCs (Deans & Moseley, 2000; Piftenger et al., 2004), marked discrepancies exist in the literature about the extent of positivity/negativity for many of these markers (Deans & Moseley, 2000; Silva et al. 2003; Piftenger et al. 2004). In particular, MSCs have been described both as positive and negative for c-kit and CD105 (c-kit$^+$: Mangi et al. 2003; CD105$^+$: Kinnaird et al. 2004b; Grinnemo et al. 2006; c-kit$^-$: Kinnaird et al., 2004b; CD105$^-$: Gojo et al. 2003). Also, the impact of surface antigen expression on differentiation potential and on the ability to secrete cardioprotective growth factors/cytokines has not been systematically investigated.

The presently disclosed subject matter provides methods of isolating a subpopulation of BM-derived adherent stem cells from a mixed population of BM-derived adherent cells. In some embodiments, the method comprises (a) providing a population of bone marrow-derived cells; (b) adhering the bone marrow-derived cells to a surface for a time sufficient to produce a mixed population of bone marrow-derived adherent stem cells on the surface; (c) isolating the mixed population of bone marrow-derived adherent stem cells; (d) contacting the mixed population of bone marrow-derived adherent stem cells with an plurality of antibodies, wherein different members of the plurality of antibodies are specific for Sca-1 or CD34, CD45, c-kit, Thy1, and CD105; and (e) isolating a subpopulation of the bone marrow-derived adherent stem cells that are Sca-1$^+$ or CD34$^+$ as well as CD45$^-$/c-kit$^-$/Thy1$^+$/CD105, whereby a subpopulation of BM-derived adherent stem cells is isolated.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from various species, some of which are summarized in Table 1.

In mice, some stem cells also express the stem cell antigen Sca-1 (GENBANK® Accession No. NP_034868), also referred to as Lymphocyte antigen Ly-6A.2.

As used herein, the term "CD45" refers to a tyrosine phosphatase, also known as the leukocyte common antigen (LCA), and having the gene symbol PTPRC. The GENBANK® database discloses amino acid and nucleic acid sequences of CD34 from various species, some of which are summarized in Table 1.

As used herein, the term "c-kit" refers to a cell surface marker found on certain stem cells and having the gene symbol KIT. The GENBANK® database discloses amino acid and nucleic acid sequences of CD34 from various species, some of which are summarized in Table 1.

As used herein, the term "Thy1" refers to a cell surface marker found on certain stem cells, and having the gene symbol THY1. Thy1 is also referred to as CD90, and these terms are used interchangeably herein. The GENBANK® database discloses amino acid and nucleic acid sequences of CD34 from various species, some of which are summarized in Table 1.

As used herein, the term "CD105" refers to a cell surface marker found on certain stem cells, and having the gene symbol CD105. The GENBANK® database discloses amino acid and nucleic acid sequences of CD34 from various species, some of which are summarized in Table 1.

TABLE 1

GENBANK ® Accession Nos. for Gene Products from Representative Species

| Gene | Species | GENBANK ® Accession Nos. Nucleic Acid | Amino Acid |
|---|---|---|---|
| CD34 | *H. sapiens* | NM_001025109 | NP_001020280 |
| | | NM_001773 | NP_001764 |
| | *M. musculus* | NM_001111059 | NP_001104529 |
| | | NM_133654 | NP_598415 |
| | *R. norvegicus* | NM_001107202 | NP_001100672 |
| | *C. l. familiaris* | NM_001003341 | NP_001003341 |
| | *F. catus* | NM_001009318 | NP_001009318 |
| | *S. scrofa* | NM_214086 | NP_999251 |
| | *B. taurus* | NM_174009 | NP_776434 |
| Sca-1/ Ly-6A.2 | *M. musculus* | NM_010738 | NP_034868 |
| CD45 | *H. sapiens* | NM_002838 | NP_002829 |
| | | NM_080921 | NP_563578 |
| | | NM_080922 | NP_563579 |
| | *M. musculus* | NM_001111316 | NP_001104786 |
| | | NM_011210 | NP_035340 |
| | *R. nonvegicus* | NM_001109890 | NP_001103360 |
| | | NM_001109889 | NP_001103359 |
| | | NM_001109887 | NP_001103357 |
| | | NM_138507 | NP_612516 |
| | *C. l. familiaris* | XM_547374 | XP_547374 |
| | *B. taurus* | XM_599431 | XP_599431 |
| c-Kit | *H. sapiens* | NM_000222 | NP_000213 |
| | | NM_001093772 | NP_001087241 |
| | *M. musculus* | NM_021099 | NP_066922 |
| Thy1 | *H. sapiens* | NM_006288 | NP_006279 |
| | *M. musculus* | NM_009382 | NP_033408 |
| CD105 | *H. sapiens* | NM_000118 | NP_000109 |
| | *M. musculus* | NM_007932 | NP_031958 |

Thus, the subpopulation of Sca-$1^+$ or $CD34^+/CD45^-$/c-$kit^-/Thy1^+/CD105^-$ stem cells represents a subpopulation of all bone marrow-derived adherent stem cells that are present in the mixed population of bone marrow-derived adherent stem cells prior to the contacting step. In some embodiments, the subpopulation of bone marrow-derived adherent stem cells are from a human, and are $CD34^+/CD45^-$/c-$kit^-/Thy1^+/CD105^-$. In some embodiments, the subpopulation of bone marrow-derived adherent stem cells are from a mouse, and are Sca-$1^+/CD45^-$/c-$kit^-/Thy1^+/CD105^-$.

The isolation of the disclosed subpopulations can be performed using any methodology that can separate cells based on expression or lack of expression of the one or more of the CD45, CD34, Sca-1, c-kit, Thy1, and CD105 markers including, but not limited to fluorescence-activated cell sorting (FACS).

The isolating step can be performed in a stepwise manner and/or concurrently. For example, the presence or absence of each marker can be assessed individually, producing two subpopulations at each step based on whether the individual marker is present. Thereafter, the subpopulation of interest can be selected and further divided based on the presence or absence of the next marker.

In some embodiments of the presently disclosed subject matter, antibodies specific for markers expressed by a cell type of interest (e.g., polypeptides expressed on the surface of a $CD34^+/CD45^-$/c-$kit^-/Thy1^+/CD105^-$ or a Sca-$1^+/CD45^-$/c-$kit^-/Thy1^+/CD105^-$ bone marrow-derived adherent stem cell) are employed for isolation and/or purification of subpopulations of BM-derived adherent stem cells that have marker profiles of interest. It is understood that based on the marker profile of interest, the antibodies can be used to positively or negatively select fractions of a population, which in some embodiments are then further fractionated.

In some embodiments, a plurality of antibodies, antibody derivatives, and/or antibody fragments with different specificities is employed. In some embodiments, each antibody, or fragment or derivative thereof, is specific for a marker selected from the group including but not limited to Ly-6A/E (Sca-1), CD34, CD45, Thy1, c-kit, and CD105. In some embodiments, cells that also express one or more genes selected from the group including but not limited to SSEA-1, Oct-4, Rev-1, and Nanog are isolated and/or purified. In some embodiments, each antibody, or fragment or derivative thereof, comprises a detectable label. Different antibodies, or fragments or derivatives thereof, which bind to different markers can comprise different detectable labels or can employ the same detectable label.

A variety of detectable labels are known to the skilled artisan, as are methods for conjugating the detectable labels to biomolecules such as antibodies and fragments and/or derivatives thereof. As used herein, the phrase "detectable label" refers to any moiety that can be added to an antibody, or a fragment or derivative thereof, that allows for the detection of the antibody. Representative detectable moieties include, but are not limited to, covalently attached chromophores, fluorescent moieties, enzymes, antigens, groups with specific reactivity, chemiluminescent moieties, and electrochemically detectable moieties, etc. In some embodiments, the antibodies are biotinylated. In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR® series of fluorescent labels available from. In some embodiments, the antibody, fragment, or derivative thereof is directly labeled with a fluorescent label such as Cy3, Cy5, or Cy7. In some embodiments, the antibodies comprise biotin-conjugated rat anti-mouse Ly-6A/E (Sca-1; clone E13-161.7), streptavidin-PE-Cy5 conjugate, rat anti-mouse anti-CD45-APCCy7 (clone 30-F11), rat anti-mouse c-kit (clone 2B8), rat anti-mouse Flk-1 (clone Avas 12α1), rat anti-mouse CD90 (clone 53-2.1), and rat anti-mouse CD105 (clone MJ7/18). All antibodies were purchased from BD Pharmingen, San Jose, Calif., United States of America. In some embodiments, the antibody, fragment, or derivative thereof is directly labeled with a fluorescent label and cells that bind to the antibody are separated by fluorescence-activated cell sorting. Additional detection strategies are known to the skilled artisan.

While FACS scanning is a convenient method for purifying subpopulations of cells, it is understood that other methods can also be employed. An exemplary method that can be used is to employ antibodies that specifically bind to one or more of Ly-6A/E (Sca-1), CD34, CD45, Thy1, c-kit, and CD105, with the antibodies comprising a moiety (e.g., biotin) for which a high affinity binding reagent is available (e.g., avidin or streptavidin). For example, a biotin moiety could be attached to antibodies for each marker for which the presence on the cell surface is desirable (e.g., Ly-6A/E (Sca-1), CD34, or Thy1), and the cell population with bound antibodies could be contacted with an affinity reagent comprising an avidin or streptavidin moiety (e.g., a column comprising avidin or streptavidin). Those cells that bound to the column would be recovered and further fractionated as desired. Alternatively, the antibodies that bind to markers present on those cells in the population that are to be removed (e.g., CD45, c-kit, and CD105) can be labeled with biotin, and the cells that do not bind to the affinity reagent can be recovered and purified further.

It is also understood that different separation techniques (e.g., affinity purification and FACS) can be employed together at one or more steps of the purification process.

A subpopulation of bone marrow-derived adherent stem cells containing the $CD34^{+}/CD45^{-}/c\text{-}kit^{-}/Thy1^{+}/CD\ 105^{-}$ or $Sca\text{-}1^{+}/CD45^{-}/c\text{-}kit^{-}/Thy1^{+}/CD105^{-}$ cells of the presently disclosed subject matter can be isolated from any subject or from any source within a subject that contains them. In some embodiments, the population of cells comprises a bone marrow sample.

The presently disclosed subject matter also provides a population of bone marrow-derived adherent stem cells isolated by the presently disclosed methods.

III. Methods and Compositions for Treatment using Bone Marrow-derived Adherent Stem Cell Subpopulations Although BM-derived MSCs can differentiate into osteogenic, chondrogenic, and adipogenic lineages, whether MSCs can differentiate into endothelial and cardiomyogenic lineages remains controversial. Moreover, the cardiac reparative benefits from unfractionated MSC therapy have been modest and variable (Tomita et al., 1999; Toma et al., 2002; Mangi et al. 2003; Kawada et al., 2004; Kinnaird et al., 2004a; Kinnaird et al. 2004b; Dai et al., 2005; Gnecchi et al., 2005; Haftan et al., 2005; Berry et al., 2006). Importantly, all of these studies with disparate results employed the conventional method of MSC isolation that involves serial culture expansion of unfractionated adherent BM cells. However, the adherent BM cells are highly heterogeneous in nature (Prockop, 1997; Majumdar et al., 1998; Phinney et al., 1999; Minguell et al., 2001; Piftenger et al., 2004; Le Blanc et al., 2006), and as preliminary data indicate, even after 72 hours of adhesion (used in multiple studies of cardiac repair; Kinnaird et al. 2004a; Tang et al., 2005), the adherent cells contain large numbers of hematopoietic cells and macrophages.

Moreover, seemingly minor changes in the method of isolation and expansion can significantly alter the expansion potential as well as the phenotype of unfractionated MSCs. Although several recent studies have examined surface markers in MSCs, disparate markers have been used (Gojo et al., 2003; Kinnaird et al. 2004b; Nagaya et al., 2005; Grinnemo et al., 2006), and "MSCs" from one study cannot be effectively compared with that of another. Thus, the variable compositions of different "MSC" populations appear to have contributed to the inconsistent results observed in several laboratories to date.

The presently disclosed subject matter thus provides in some embodiments a method for treating an injury to a tissue or organ in a subject, the method comprising administering to the subject a pharmaceutical composition, wherein the pharmaceutical composition comprises a plurality of isolated $CD34^{+}/CD45^{-}/c\text{-}kit^{-}/Thy1^{+}/CD105^{-}$ or $Sca\text{-}1^{+}/CD45^{-}/c\text{-}kit^{-}/Thy1^{+}/CD105^{-}$ bone marrow-derived adherent stem cells in a pharmaceutically acceptable carrier, in an amount and via a route sufficient to allow at least a fraction of the members of the subpopulation to engraft the tissue and differentiate therein, whereby the injury is treated.

As used herein, the phrase "treating an injury to a tissue or organ in a subject" refers to both intervention designed to ameliorate the symptoms of causes of the injury in a subject (e.g., after initiation of the disease process) as well as to interventions that are designed to prevent the disease from occurring in the subject. Stated another way, the terms "treating" and grammatical variants thereof are intended to be interpreted broadly to encompass meanings that refer to reducing the severity of and/or to curing a disease, as well as meanings that refer to prophylaxis. In this latter respect, "treating" refers to "preventing" or otherwise enhancing the ability of the subject to resist the disease process.

III.A. Formulations

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

III.B. Administration

Suitable methods for administration the cells of the presently disclosed subject matter include, but are not limited to intravenous administration and delivery directly to the target tissue or organ. In some embodiments, the method of administration encompasses features for regionalized delivery or accumulation of the cells at the site in need of treatment. In some embodiments, the cells are delivered directly into the tissue or organ to be treated. In some embodiments, selective delivery of the presently disclosed cells is accomplished by intravenous injection of cells, where they home to the target tissue or organ and engraft therein.

III.C. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Materials and Methods Employed in the Examples

Figure 9:
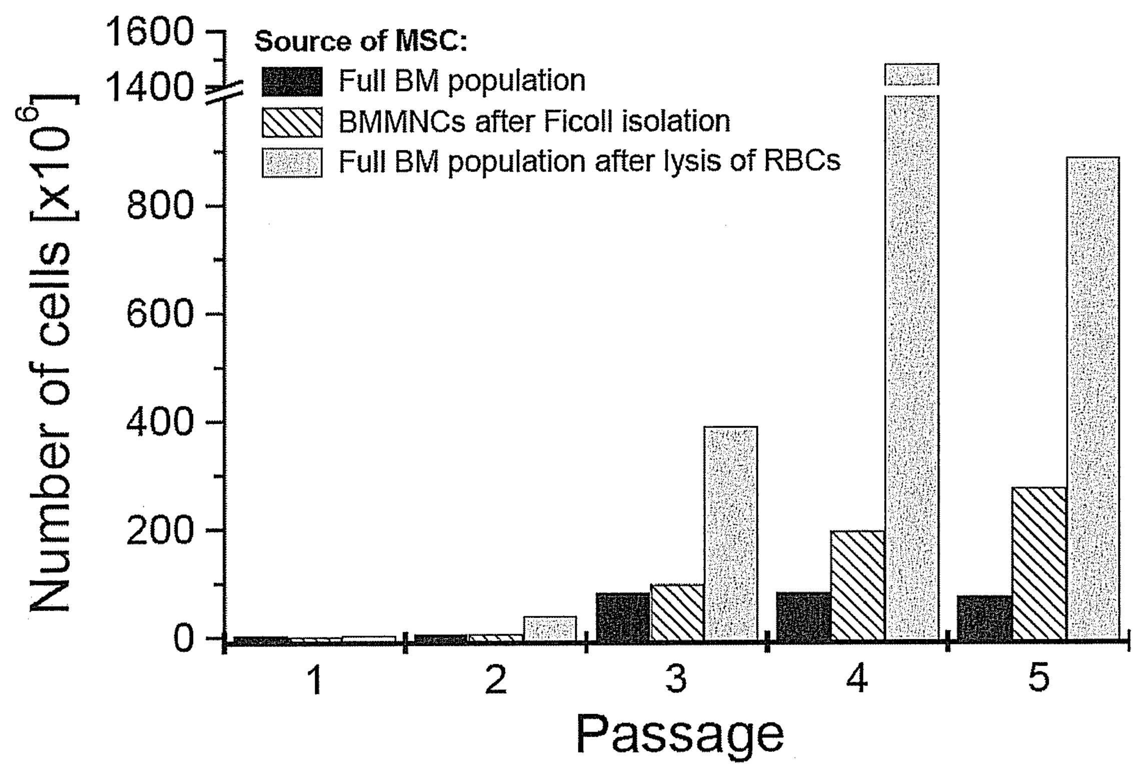
FIG. 9 is a bar graph showing that DMEM/F-12 induces greater expansion of MSCs compared with that in MESENCULT® (see FIG. 1).

Isolation of unfractionated MSCs by adherence to plastic. Adult mice (C57BL/6) were euthanized, the long and hip bones removed and placed in DMEM/F-12, and marrow pulp extracted via repeated irrigation using a 21-gauge needle. Cells were triturated by gentle pipetting and red blood cells (RBCs) lysed by the addition of a 0.8% solution of $NH_4Cl$. The method of lysis of RBCs was used because this method yielded superior expansion potential of adherent MSCs (see e.g., FIGS. 1 and 9). After washing in medium, cells were plated in 10-cm diameter uncoated plates ($1\times10^6$ cells/$cm^2$). Non-adherent cells were removed after 72 hours. Cells were allowed to adhere for 72 hours so that more cells with primitive behavior would be retained.

Figure 12:
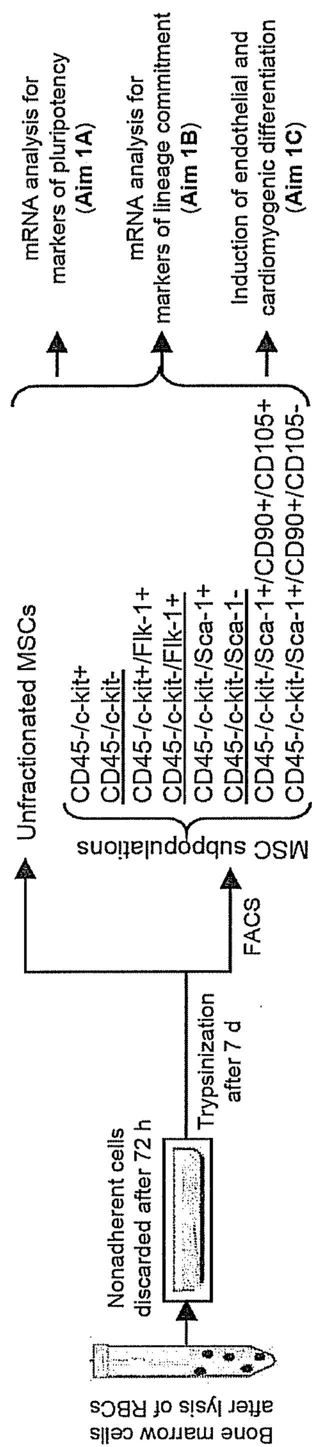
FIG. 12 is a map of an exemplary protocol for performing quantitative assessment of mRNA expression, differentiation, and growth factor secretion for various subpopulations of cells of the presently disclosed subject matter.

Isolation of antigenically-defined MSC subpopulations by flow cytometry. Unfractionated adherent MSCs isolated as per the above were trypsinized at 7 days. The impact of antigen expression on MSC characteristics isolated at the same time before expansion was directly compared. However, to perform quantitative assessment of mRNA expression, differentiation, and growth factor secretion, an adequate number of cells are required for each of the 8 subpopulations (see FIG. 12).

Figure 2:
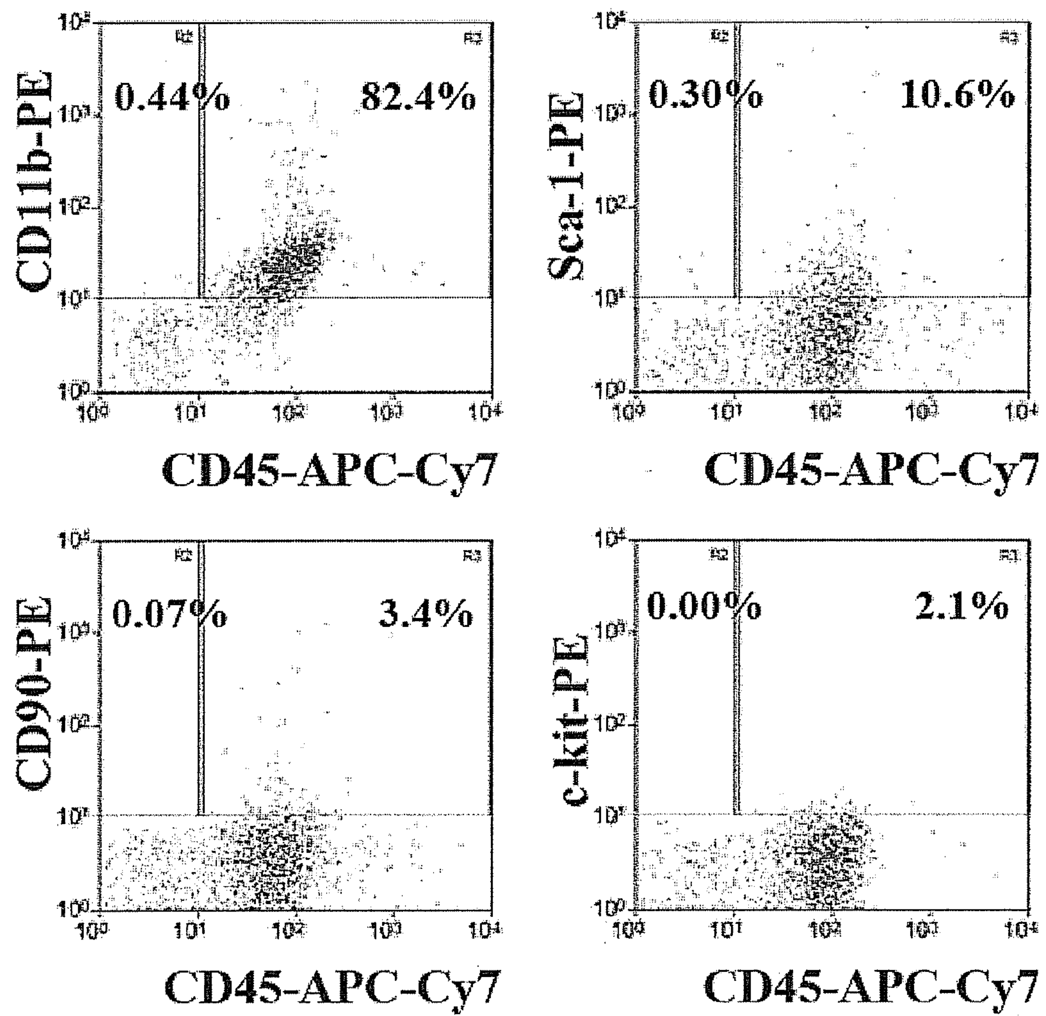
FIG. 2 is a series of FACS plots showing that analysis of surface antigen expression in adherent cells after plating for 72 hours shows predominantly $CD45^+$ hematopoietic cells and $CD11b^+$ macrophages. Non-hematopoietic ($CD45^-$) cells positive for Sca-1, c-kit, and Thy1/CD90 (R2 region) are present in very low numbers (0.00-0.44% of adherent cells).
Figure 5:
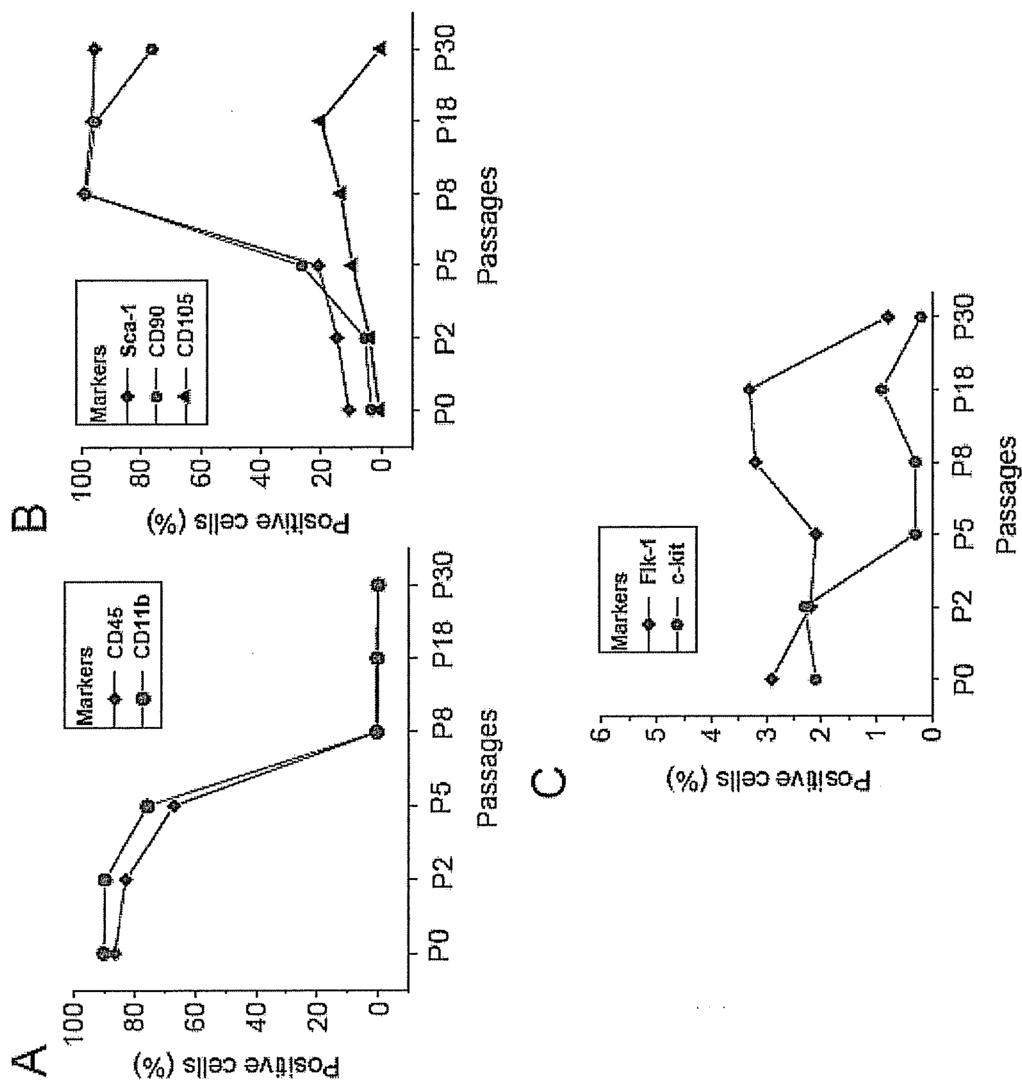
FIGS. 5A-5C are a series of graphs of serial flow cytometric analyses showing marked changes in expression of CD45 and CD11b FIG. 5A); Sca-1, CD90, and CD105 (FIG. 5B); and Flk-1 and c-kit (FIG. 5C) surface antigens in unfractionated MSCs during serial passages.
FIGS. 5D-5J are a series of flow cytometry plots showing changes of expression between passages 2 and 30, inclusive, of Sca-1 (FIG. 5D), CD45 (FIG. 5E), c-kit (FIG. 5F), Thy1/CD90 (FIG. 5G), CD105 (FIG. 5H), Flk-1 (FIG. 5I), and CD11b (FIG. 5J).

In preliminary experiments, surface antigen analysis in MSCs after 72 hours revealed considerable contamination with hematopoietic cells and macrophages with very low numbers of non-hematopoietic cells expressing markers relevant for nonhematopoietic stem/progenitors (see FIG. 2). On the other hand, after 8 passages, the numbers of Sca-$1^-$ (~0.9% of all cells) and c-$kit^+$ (~0.3% of all cells) cells were very low (see FIG. 5), which precluded isolation of adequate number of cells for several subpopulations in FIG. 12.

Therefore, all subpopulations were isolated after 7 days, which allowed an adequate number of cells to be isolated in all subpopulations. MSCs were stained for CD45, c-kit, Flk-1, Sca-1, Thy1/CD90, and CD105 using directly conjugated monoclonal antibodies (BD Biosciences, San Jose, Calif., United States of America). Combinations of surface antigens (FIG. 12) were used to obtain MSC subpopulations by multicolor FACS. The purities of sorted cells were also checked to ensure >95% purity.

Example 1

Analysis of MSC Isolation Under Different Conditions

Whether the expansion potential of adherent MSCs isolated after different methods are similar in the same medium was investigated. Adherent MSCs obtained after plating whole BM cells, BM cells obtained via lysis of RBCs (by 0.8% $NH_4Cl$ solution), and via Ficoll density centrifugation were expanded in MESENCULT® culture medium (Stem Cell Technologies Inc., Vancouver, British Columbia, Canada), and the total number of cells was estimated during each passage. Unfractionated MSCs obtained via adherence after lysis of RBCs exhibited greatest expansion potential (see FIG. 1), indicating that depending on the method of purification, MSCs exhibited differential expansion rates in the same medium, suggesting heterogeneity between even unfractionated MSCs.

Example 2

Analysis of Adherent Cells after 72 Hours

In typical isolation protocols, BM cells are allowed to adhere for variable lengths of time, ranging from overnight to 72 hours. Macrophages are generally one of the earliest cells to adhere; while cells with a primordial phenotype might not adhere easily, and the cell population that adheres quickly might not represent the ideal cell population for cardiac repair.

In preliminary analyses, adherent cells contained large numbers of hematopoietic ($CD45^+$) cells and macrophages ($CD45^+/CD11b^+$) after 72 hours. Moreover, non-hematopoietic ($CD45^-$) cells rarely expressed c-kit, Sca-1, and CD90 (see FIG. 2), markers that are associated with stem/progenitor cells. Based on these observations, although non-adherent cells were discarded after 72 hours, MSC subpopulations were sorted after 7 days of culture. This method for the delayed isolation of MSC subpopulations allowed for the isolation of cells with endothelial and cardiomyogenic differentiation potential.

Example 3

Figure 3:
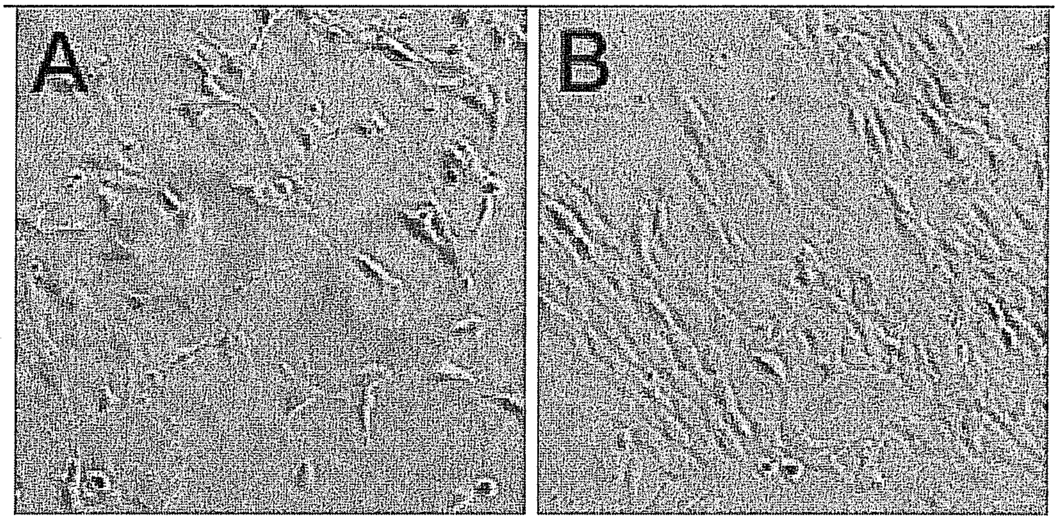
FIGS. 3A and 3B are photomicrographs showing that the unfractionated adherent MSC population continues to be morphologically heterogeneous even after 28 passages (see FIG. 3A), while the $CD45^-/ckit^-/CD90^+/Sca\text{-}1^+/CD105^-$ subpopulation appears homogeneous after 9 passages (FIG. 3B) or earlier.

Antigenically-Defined MSC Subpopulation Exhibited a Homogenous Morphology During Expansion Following adherence, MSCs were cultured in MESENCULT®. After 7 days, MSCs were tested for expression of for CD45, c-kit, Flk-1, Sca-1, CD90, and CD105 using specific antibodies (rat anti-mouse CD45 (clone 30-F11), rat anti-mouse c-kit (clone 2B8), rat anti-mouse Flk-1 (clone Avas 12$\alpha$1), rat anti-mouse Sca-1 (clone E13-161.7), rat anti-mouse CD90 (Thy1, clone 53-2.1) and rat anti-mouse CD105 (clone MJ7/18), all of which were purchased from BD Pharmingen of San Jose, Calif., United States of America), and antigenically-defined distinct MSC subpopulations were sorted by FACS using a MOFLO™ High-Performance Cell Sorter (Dako North America, Inc., Carpinteria, Calif., United States of America, using Summit 4.3 software). Unfractionated MSCs were morphologically heterogeneous at isolation, and this morphological heterogeneity persisted even after 28 passages (see FIG. 3A). In contrast, CD45/c-kit$^-$/Sca-1$^+$/CD90$^+$/CD105$^-$ MSCs exhibited a homogenous morphology early during expansion (see FIG. 3B), indicating that the analysis of surface antigen expression can be used to isolate MSC subpopulations with greater morphological homogeneity. These results also indicated that the heterogeneity of unfractionated MSCs cannot be eliminated simply by prolonged expansion.

Example 4

Figure 4:
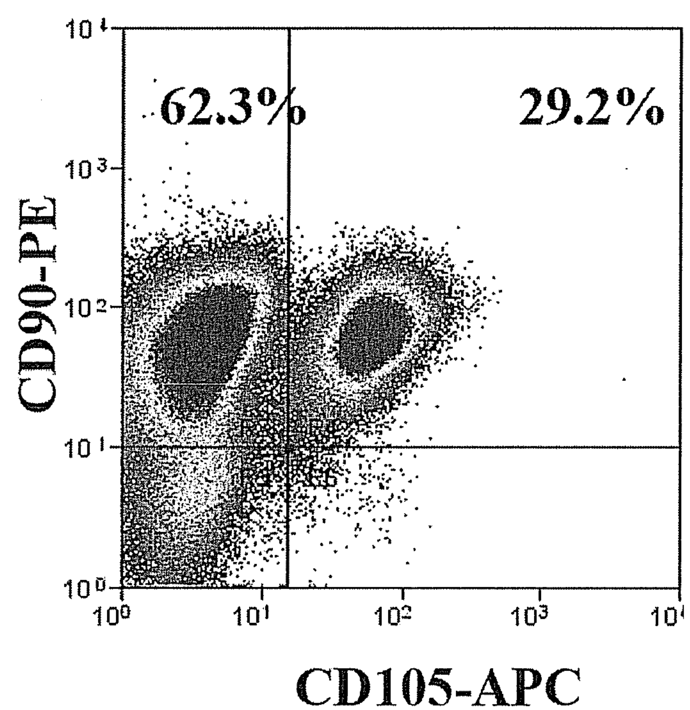
FIG. 4 is a FACS plot showing that considerable heterogeneity with respect to surface antigen (CD90 and CD105) expression persists during expansion of unfractionated adherent MSCs after 16 passages.

Unfractionated MSCs Exhibit Persistent Heterogeneity in Surface Antigen Expression During Expansion Unfractionated MSCs were isolated by adherence and expanded during serial passages. During each passage, MSCs were stained and analyzed by flow cytometry. Unfractionated MSCs were antigenically heterogeneous during early stages of culture, and this heterogeneity persisted during expansion. For example, even after 16 passages, only 63% of culture-expanded unfractionated MSCs were positive for CD90, and 29% were positive for CD105 (see FIG. 4).

Thus, although culture-expanded MSCs are referred to as a homogeneous population, the experiments disclosed herein indicated that unfractionated MSCs continued to remain heterogeneous for surface antigen expression during expansion.

Example 5

Changes in Expression of Surface Antigens During Expansion

Unfractionated MSCs were isolated and expanded in MESENCULT®. Serial analysis of surface antigen expression by flow cytometry revealed a marked decline in hematopoietic cells (CD45$^+$) and macrophages (CD11b$^+$) during expansion (see FIG. 5A), indicating that the "MSC" population used in several in vivo studies of cardiac repair that used cells after only a few passages (see Dai et al. 2005; Tang et al., 2005; Freyman et al. 2006; Wang et al., 2006) perhaps contained macrophages and hematopoietic cells. The expression of Sca-1 and CD90, which are markers of stem/progenitor cells, increased gradually during expansion, while the increase in CD105 expression was followed by a decline (see FIG. 5B). The expression of two other important markers of stem/progenitor cells, Flk-1 and c-kit, decreased during expansion (see FIG. 5C).

Figure 5D:
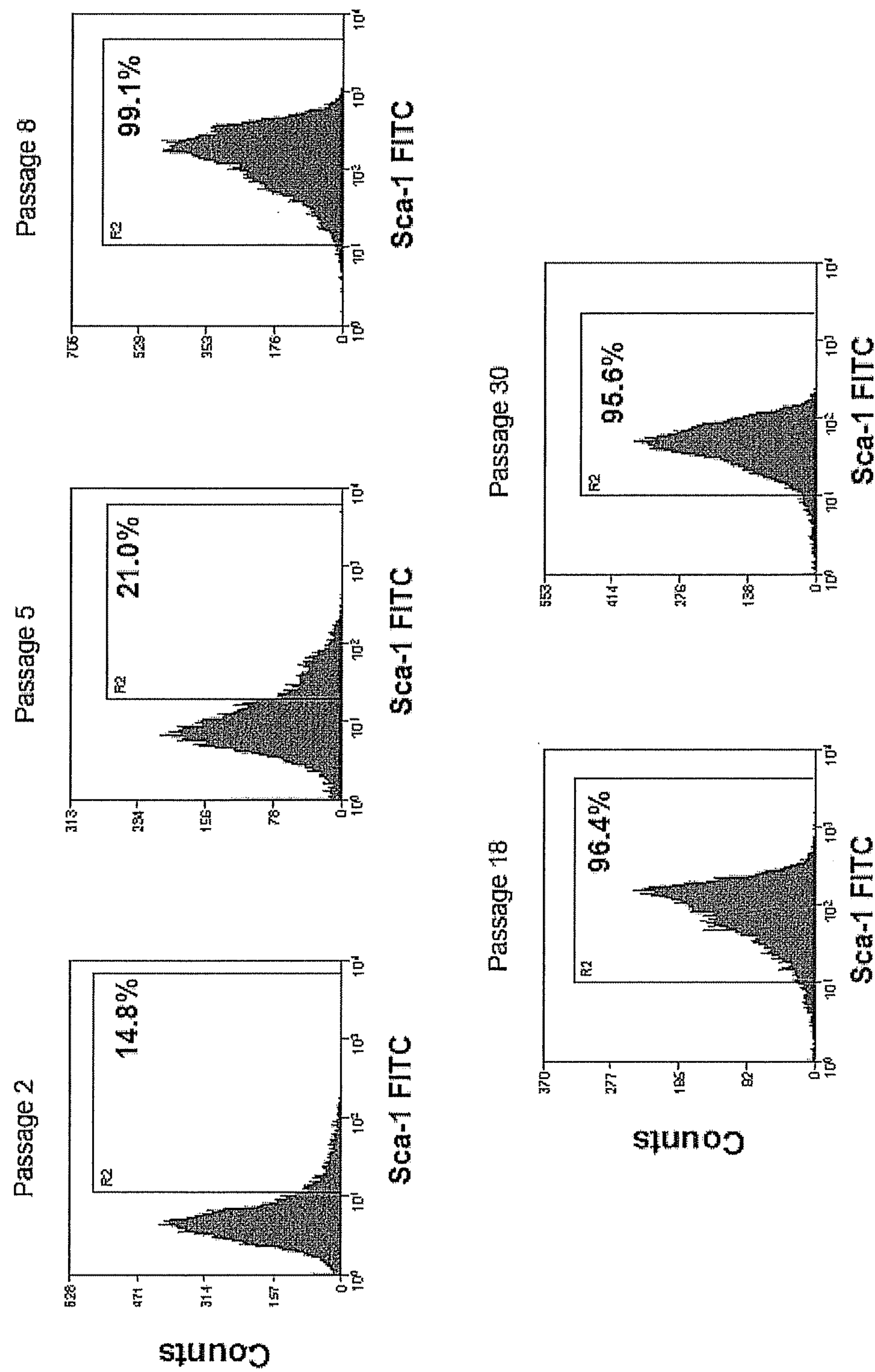
Figure 5E:
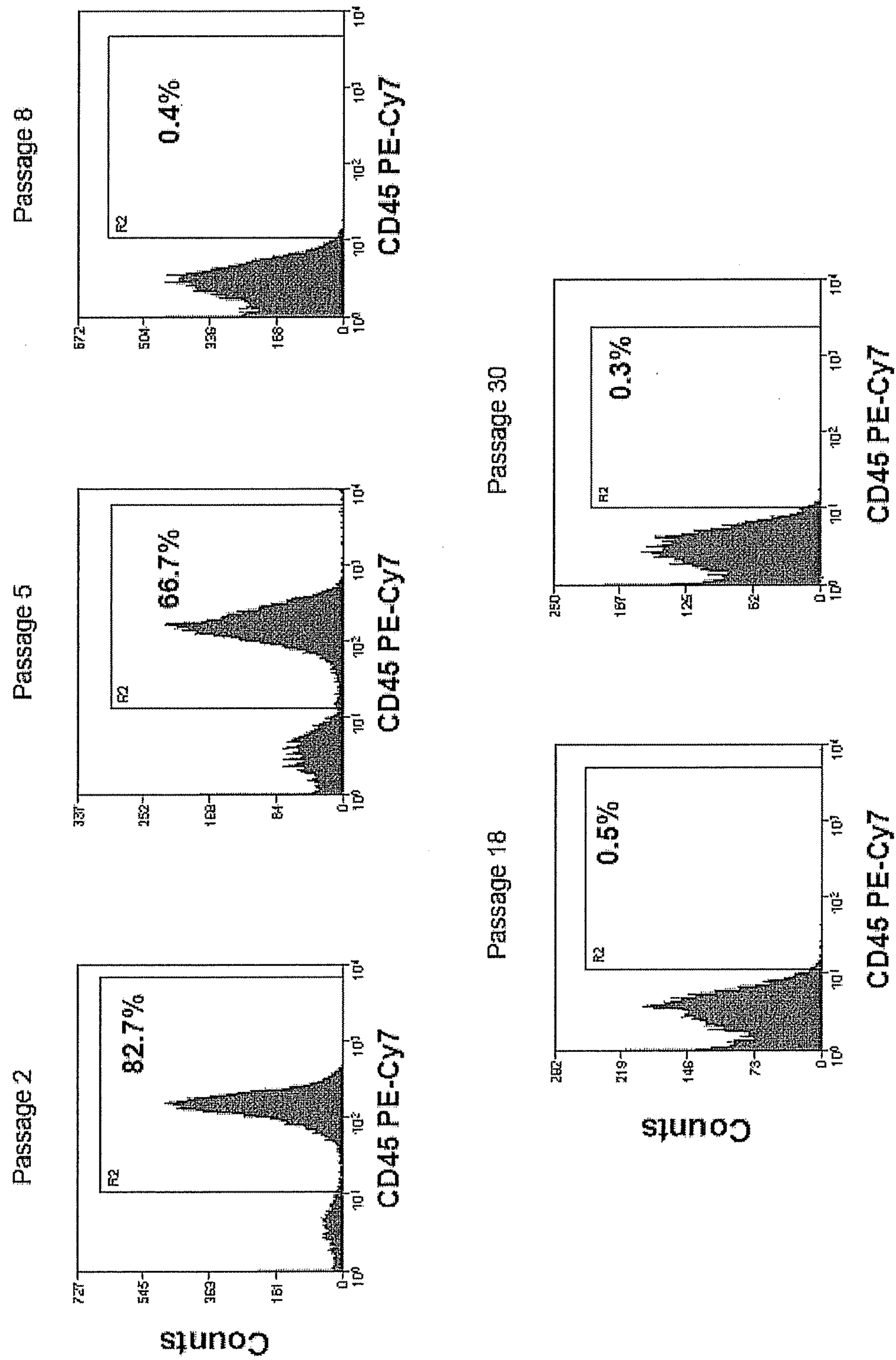
Figure 5F:
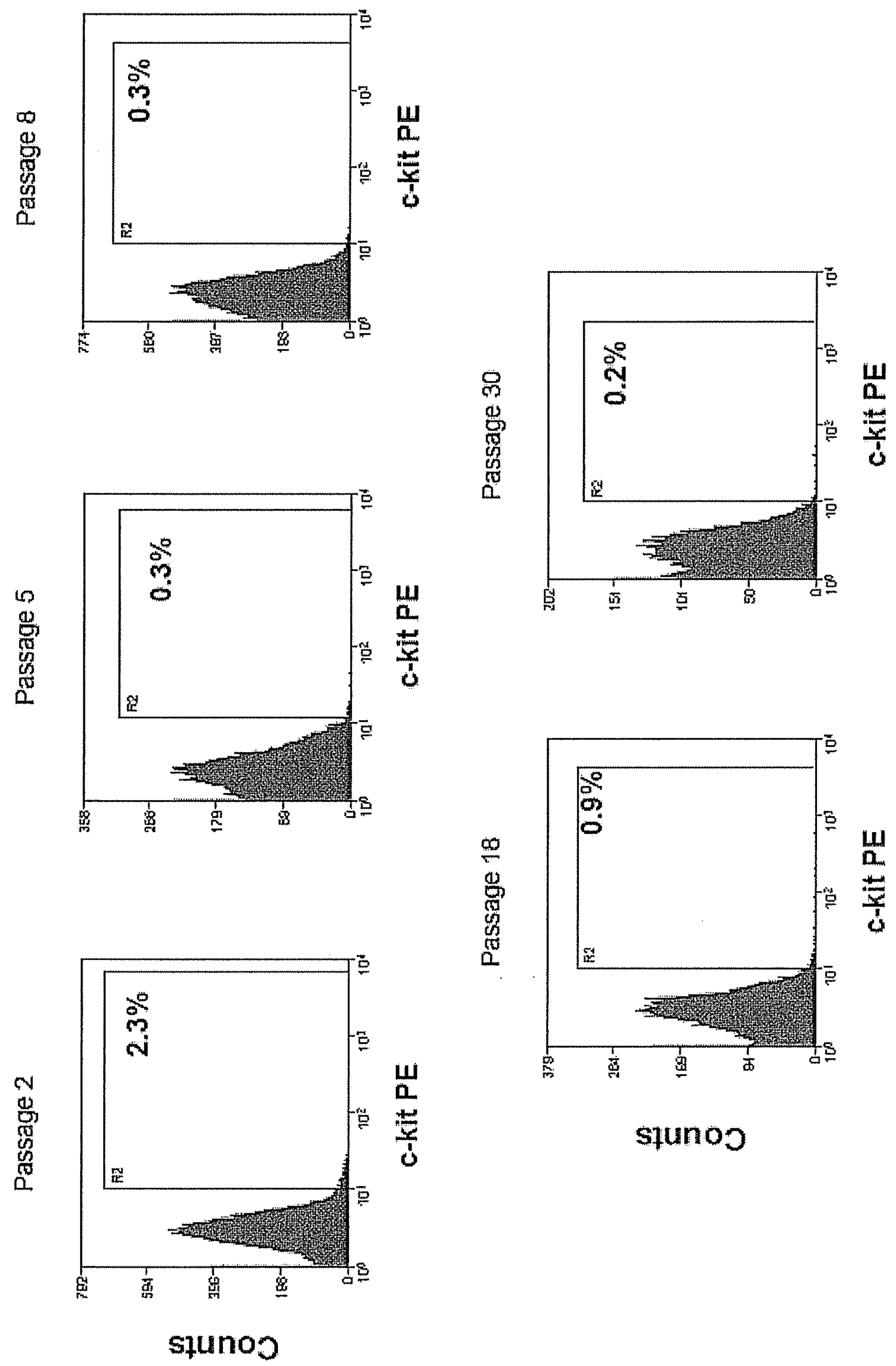
Figure 5G:
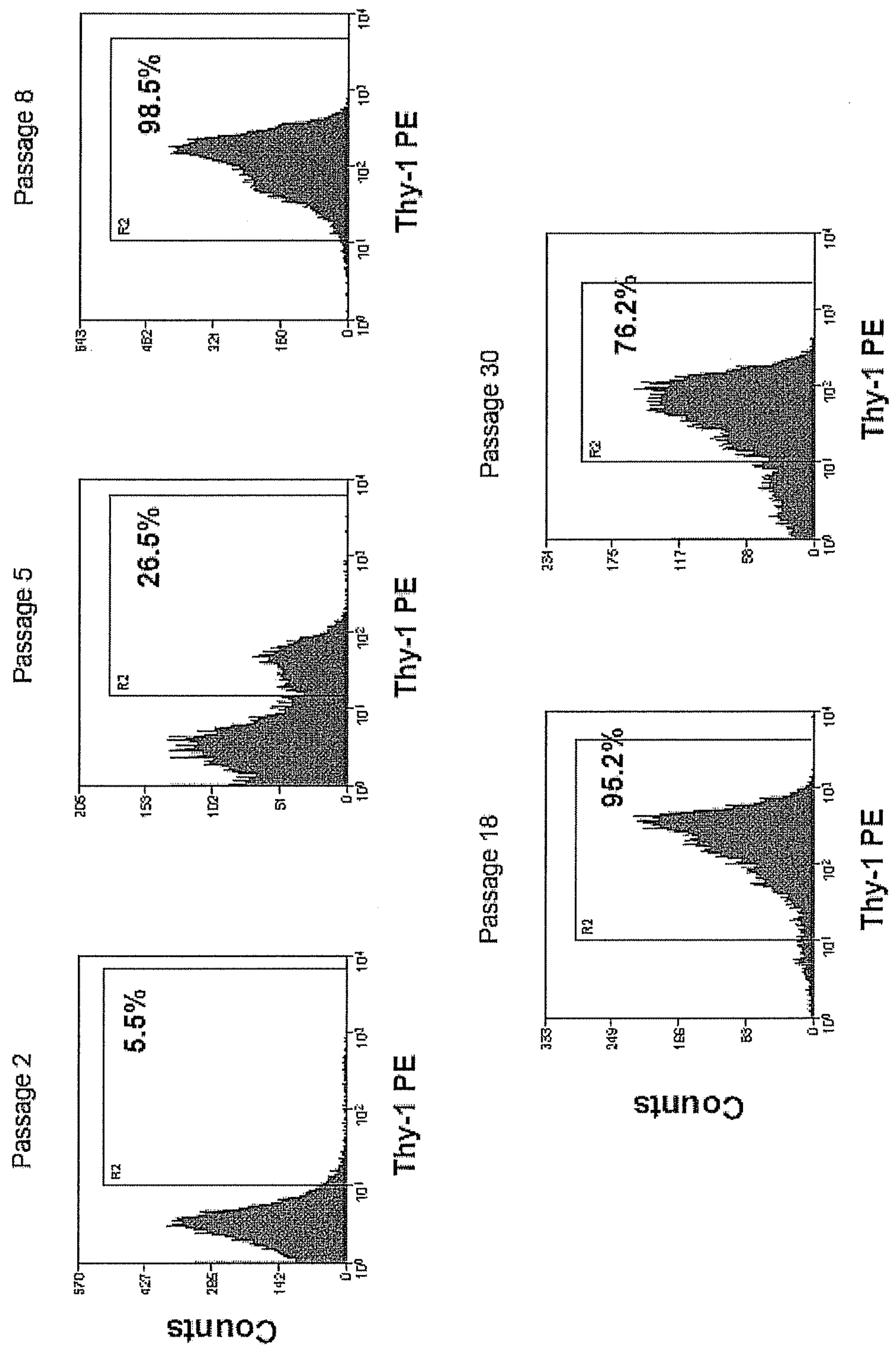
Figure 5H:
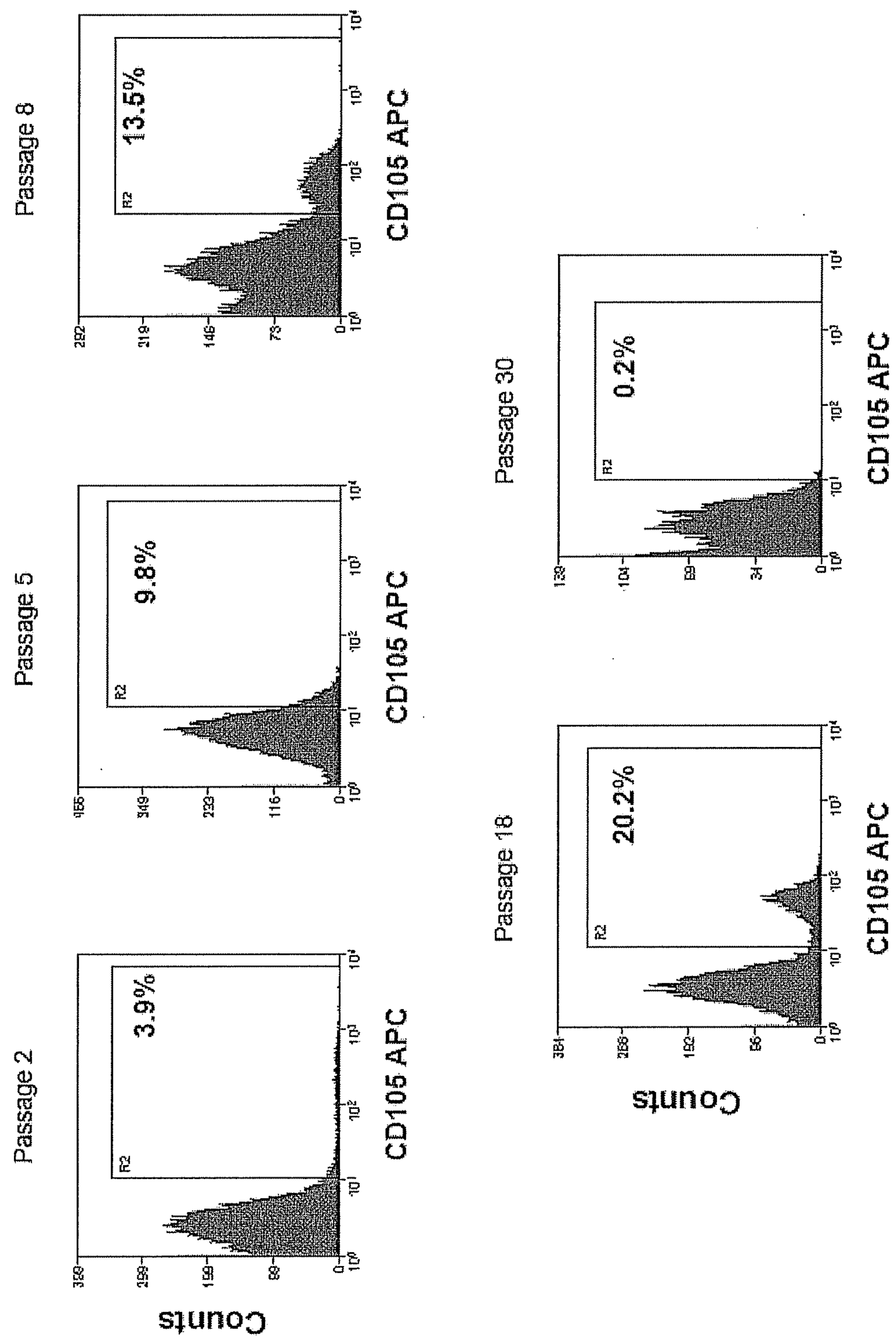
Figure 5I:
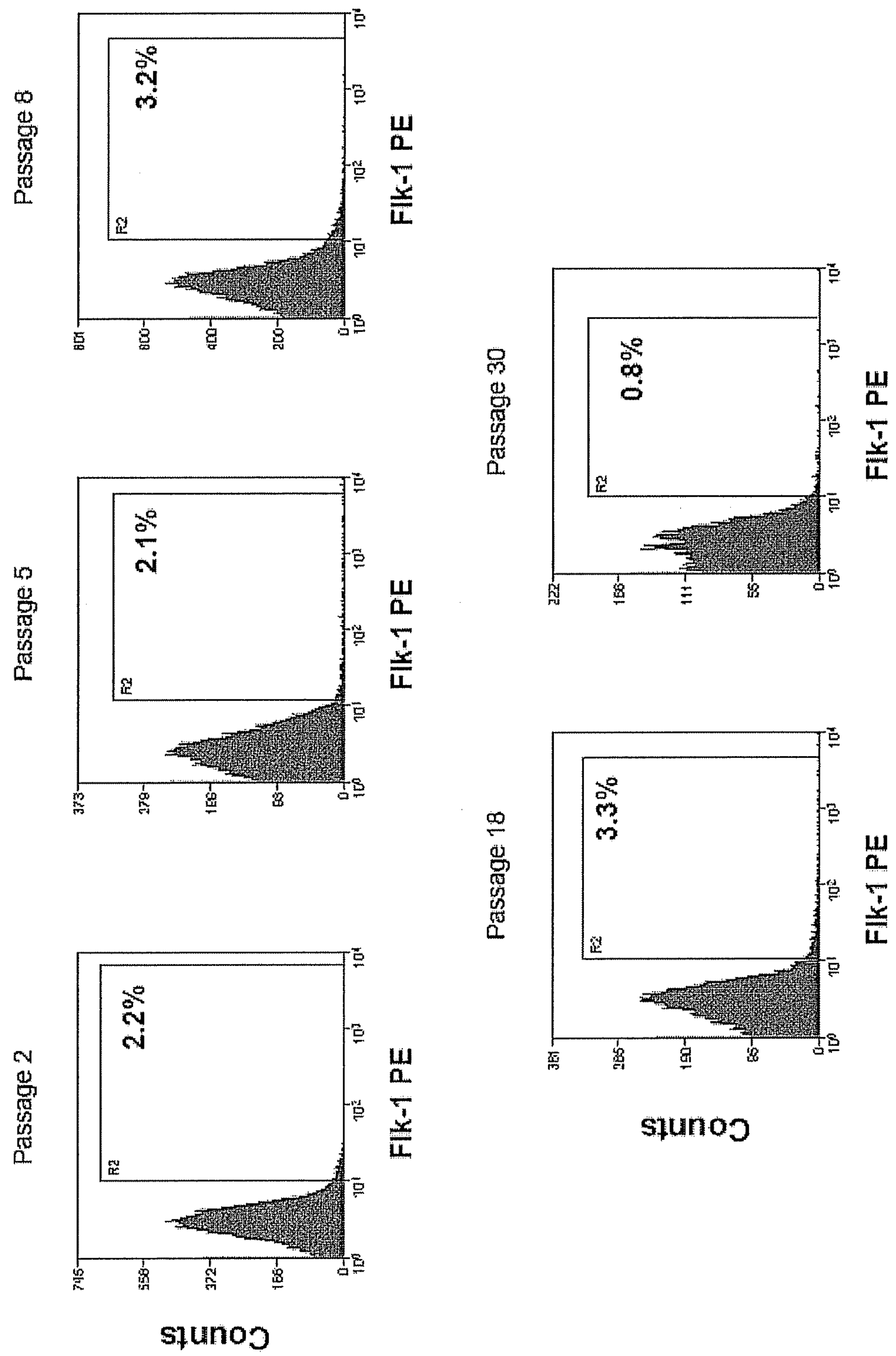
Figure 5J:
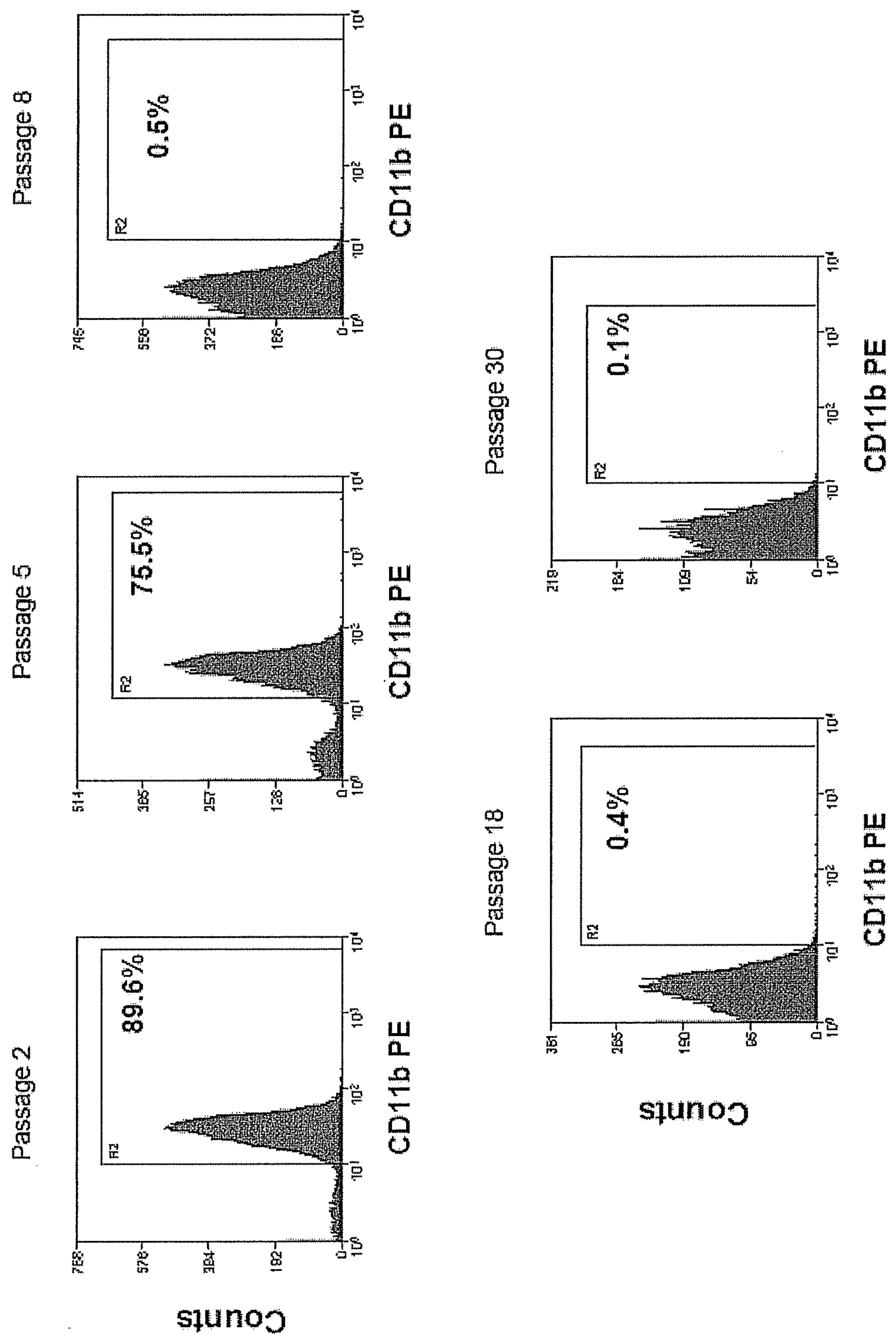

Additionally, during each passage, an aliquot of cells (approx. 100,000) were stained with directly flourochrome-conjugated specific antibodies against Sca-1, CD45, c-kit, Thy-1, CD105, Flk-1, and CD11b. The expression of these antigens was serially assessed quantitatively by flow cytometric analysis. The data presented in FIGS. 5D-5J demonstrated that during passages 2 through 30, the expression of antigens change considerably. Specifically, it was noted that over this time, Sca-1 expression progressively increased (see FIG. 5D), CD45 expression decreased (see FIG. 5E), c-kit expression decreased (see FIG. 5F), Thy1CD90 expression increased followed by minor decline in levels (see FIG. 5G), CD105 expression gradually increased and then decreased (see FIG. 5H), Flk-1 expression decreased (see FIG. 5I), and CD11b expression decreased sharply (see FIG. 5J).

These data suggested the importance of accurate characterization of surface antigen expression during MSC expansion. These observations also emphasized the need for establishing optimal culture conditions to achieve MSC expansion with no or minimal changes in surface antigen expression, genetic composition, and differentiation potential.

Example 6

Figure 6:
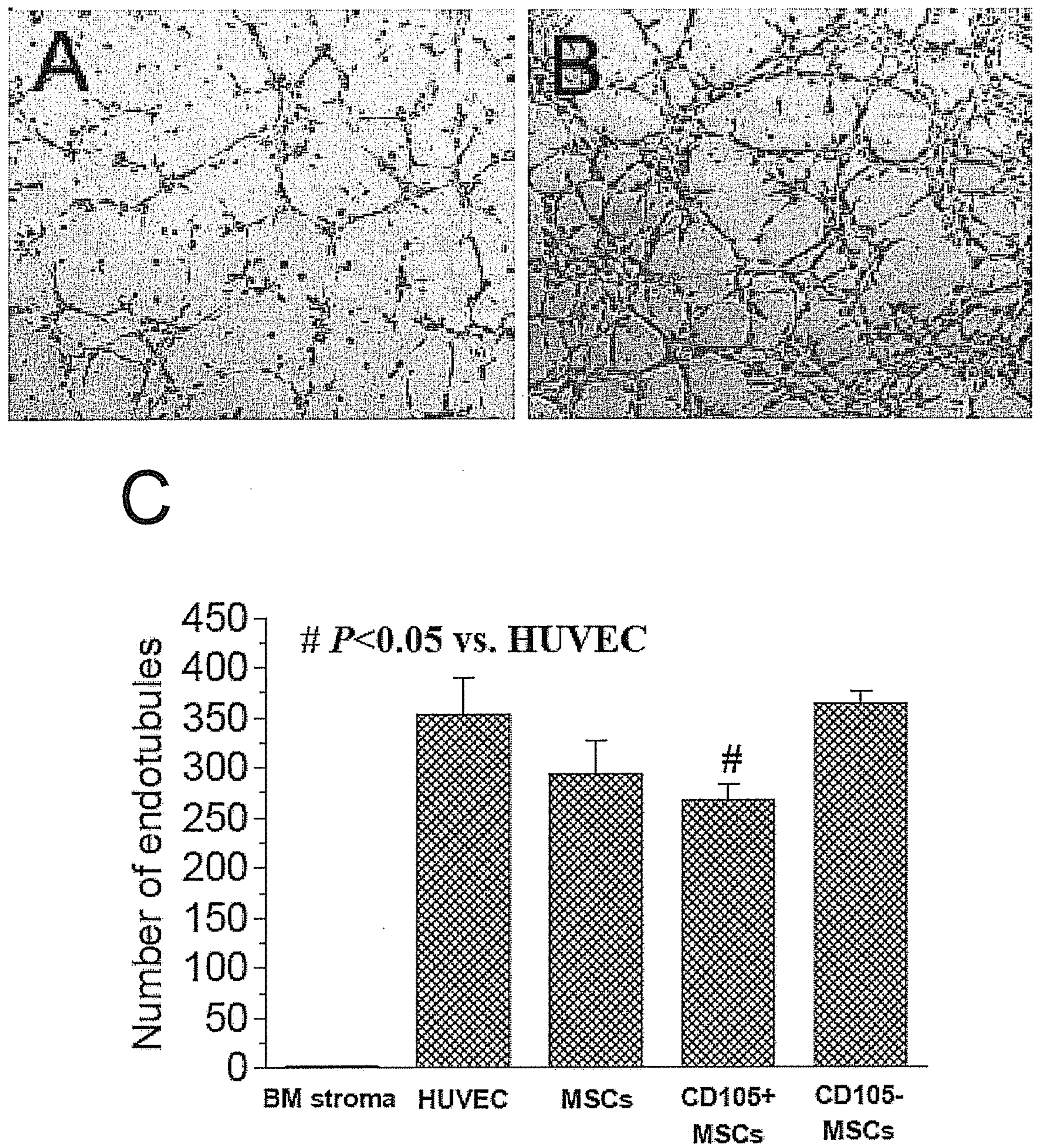
FIGS. 6A-6C demonstrate quantitative assessment of endotubule formation (FIG. 6C) on MATRIGEL™ by unfractionated (FIG. 6A) and $Sca\text{-}1^+/CD45^-/ckit^-/CD90^+/CD105^-$ MSCs (FIG. 6B).

CD457c-kit$^-$/Sca-1$^+$/CD90$^+$/CD105$^-$ MSCs Exhibit Enhanced Endotubule Formation In Vitro Unexpanded unfractionated MSCs and antigenically-defined MSC subpopulations isolated by FACS were plated on MATRIGEL™-coated plates in EBM medium supplemented with EGM-MV (Cambrex Corp., East Rutherford, N.J., United States of America). After 6 hours, 10 transmission images (FIG. 6) covering the entire plate were acquired from each plate with an inverted microscope (Axiovert, Carl Zeiss, Inc., Thornwood, N.Y., United States of America). Endotubules were counted on printouts of images. Amongst the subpopulations examined thus far, compared with the unfractionated MSCs, the CD45$^-$/c-kit$^-$/Sca-1$^+$/CD90$^+$/CD105$^-$ MSCs showed a greater number of endotubule formation (see FIG. 6).

These results indicated that as compared to unfractionated MSCs, the antigenically-defined MSC subpopulation exhibited greater angiogenic potential.

Example 7

Figure 7:
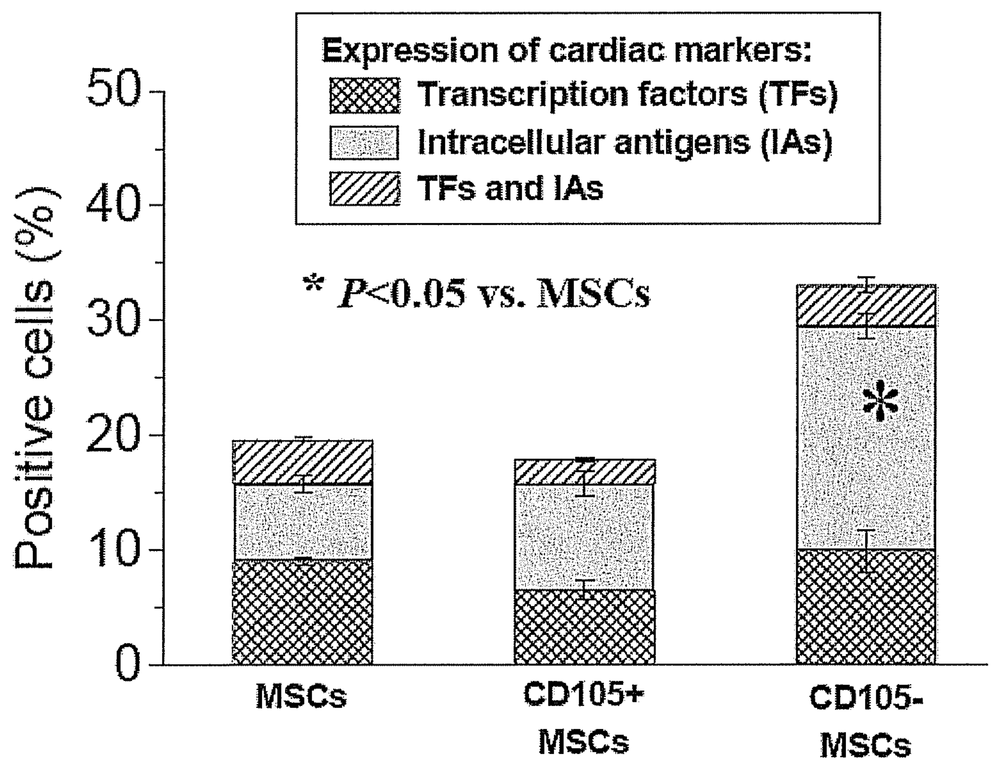
FIG. 7 is a bar graph showing a quantitative assessment of enhanced cardiomyogenic differentiation in $Sca\text{-}1^+/CD45^-/ckit^-/CD90^+/CD105^-$ MSCs compared with unfractionated adherent MSCs and $Sca\text{-}1^+/CD45^-/ckit^-/CD90^+/CD105^+$ MSCs.

Cardiomyogenic Differentiation Potential of CD45$^-$/c-kit$^-$/Sca-1$^+$/CD90$^+$/CD105$^-$ MSCs Unexpanded unfractionated MSCs and antigenically-defined MSC subpopulations isolated by FACS were subjected to cardiomyogenic differentiation induction. Cardiomyogenic medium consisted of DMEM/F-12, 10% FBS, IGF-1, Dynorphin B, insulin, and TGF-β1 (Zuba-Surma et al. 2006). Cardiomyogenic differentiation commitment was examined by immunocytochemical staining for cardiac-specific markers (GATA-4, Nkx2.5, cardiac myosin heavy chain, troponin T, and α-sarcomeric actin). Among the subpopulations examined, the CD45$^-$/c-kit$^-$/Sca-1$^+$/CD90$^+$/CD105$^-$ MSCs showed greater cardiomyocytic lineage commitment as compared with the unfractionated MSCs as evidenced by expression of cardiac-specific transcription factors and structural proteins (see FIG. 7). These results indicated that compared with unfractionated MSCs, the presently disclosed antigenically-defined MSC subpopulation exhibited greater cardiomyogenic potential.

Example 8

Figure 8:
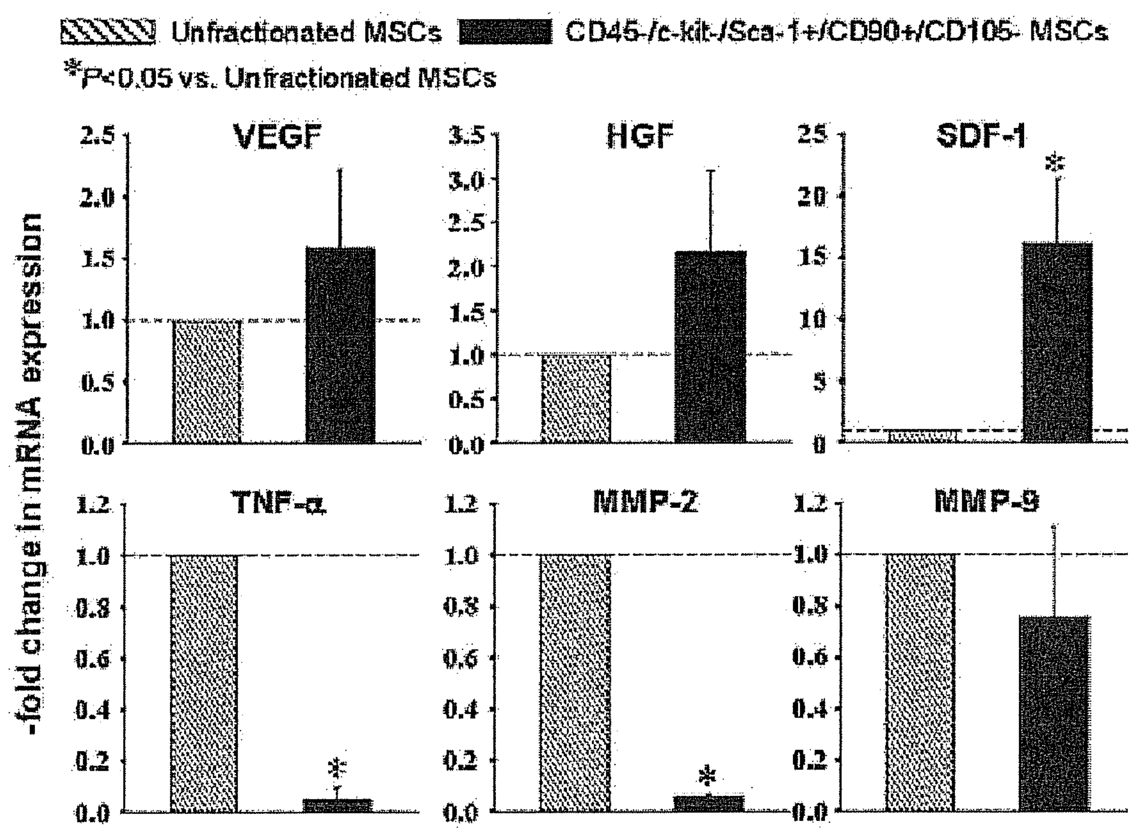
FIG. 8 is a series of bar graphs showing expression of VEGF, HGF, SDF-1, TNF-α, MMP-2, and MMP-9 mRNAs in $CD45^-/c\text{-}kit^-/Sca\text{-}1^+/CD90^+/CD105^-$ MSCs compared with unfractionated MSCs. Data are mean±SEM.

CD45$^-$/c-kit$^-$/Sca-1$^+$/CD90$^+$/CD105$^-$ MSCs are Enriched in Factors Beneficial for Cardiac Repair mRNA expression of several molecules known to play beneficial and detrimental roles during post-infarct cardiac remodeling was quantitatively examined in unfractionated MSCs and antigenically-defined MSC subpopulations by real-time RT-PCR. Compared with unfractionated MSCs, the CD45$^-$/c-kit$^-$/Sca-1$^+$/CD90$^+$/CD105$^-$ MSCs expressed greater mRNA levels of VEGF, HGF, and SDF-1 (see FIG. 8). Also, the expression levels of TNF-α, MMP-2, and MMP-9 were lower in CD45$^-$/c-kit$^-$/Sca-1$^+$/CD90$^+$/CD105$^-$ MSCs compared with unfractionated MSCs (see FIG. 8). Importantly, VEGF and HGF are thought to exert angiogenic and antiapoptotic actions (Leung et al., 1989; Rosen et al., 1993; Nicosia et al. 1994), while SDF-1 appears to be involved in the recruitment of circulating progenitors, thereby facilitating cardiac repair (Lapidot, 2001; Askari et al. 2003; Abbott et al. 2004). In contrast, expression of TNF-α in the infarcted LV is known to be detrimental (Oral et al., 1995; Ono et al., 1998; Irwin et al., 1999). Similarly, MMP-2 and MMP-9 aggravate post-infarct remodeling via collagen degradation (Li et al., 2000), and anti-MMP interventions result in improved outcomes after MI (Rohde et al., 1999; Ducharme et al. 2000; Creemers et al., 2001).

Thus, the results presented herein support the hypothesis that antigenically-selected MSCs are superior substrates for cellular therapy for cardiac repair after MI by virtue of a favorable secretory profile.

Example 9

The Expansion Culture Medium Influences the Rate of MSC Expansion

To determine the impact of medium on the expansion rate of unfractionated MSCs, freshly isolated unfractionated MSCs were plated in two different primary culture media: (1) DMEM/F-12 with 10% FBS; and (2) MESENCULT®). Cells were passaged when the confluence reached approximately 70%, and the total number of cells was estimated during each passage. DMEM/F-12 (FIG. 9) induced considerably greater expansion of respective MSCs as compared with MESENCULT® (see FIG. 1), which indicated that although these primary media are used commonly and the results are considered comparable, these media exerted different influences on MSC proliferation. These results underscored the importance of optimizing the composition of culture conditions for MSC expansion.

Example 10

Figure 10A:
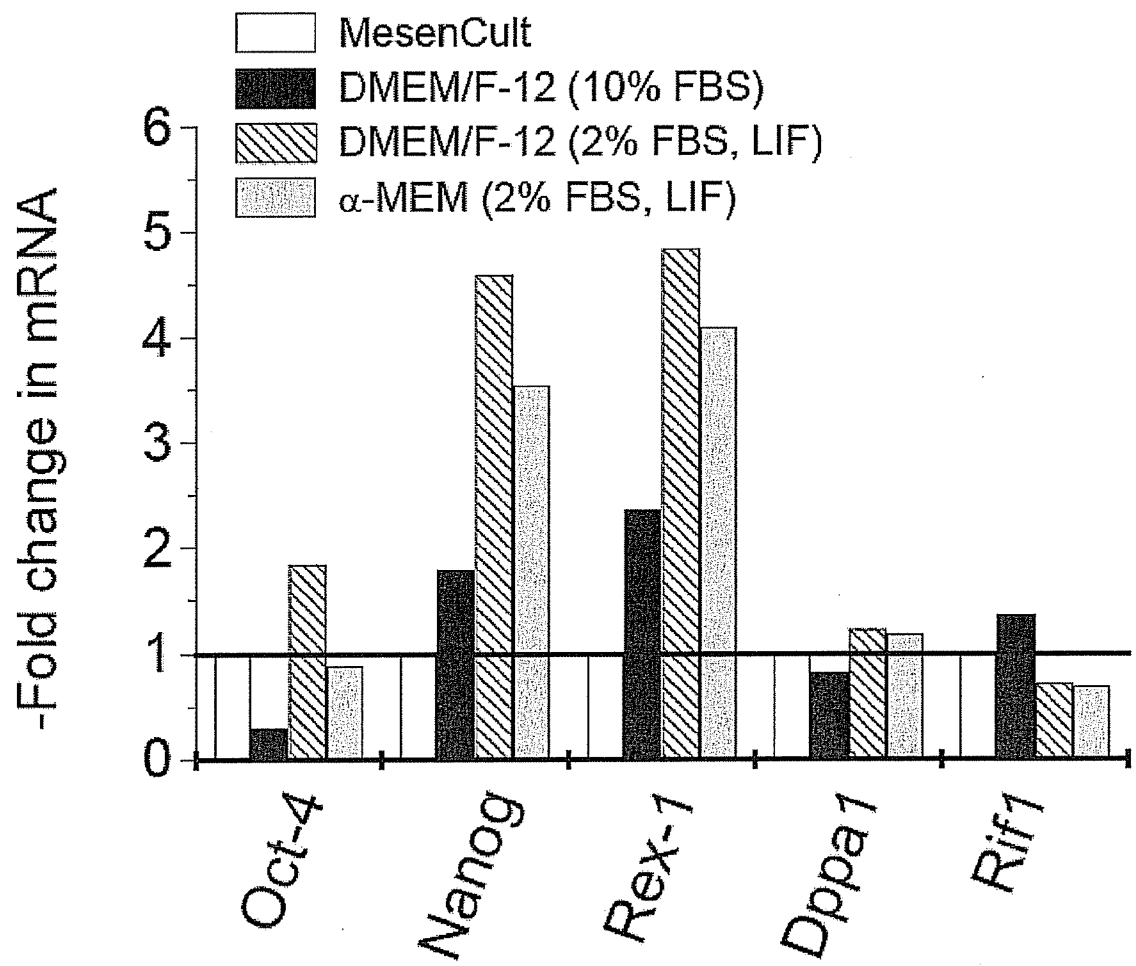
FIGS. 10A and 10B are bar graphs showing changes in mRNA expression for markers of pluripotency during expansion of unfractionated MSCs in different media at passages 1 and 2, respectively. Fold change was calculated compared with mRNA expression in MESENCULT® culture medium.
Figure 10B:
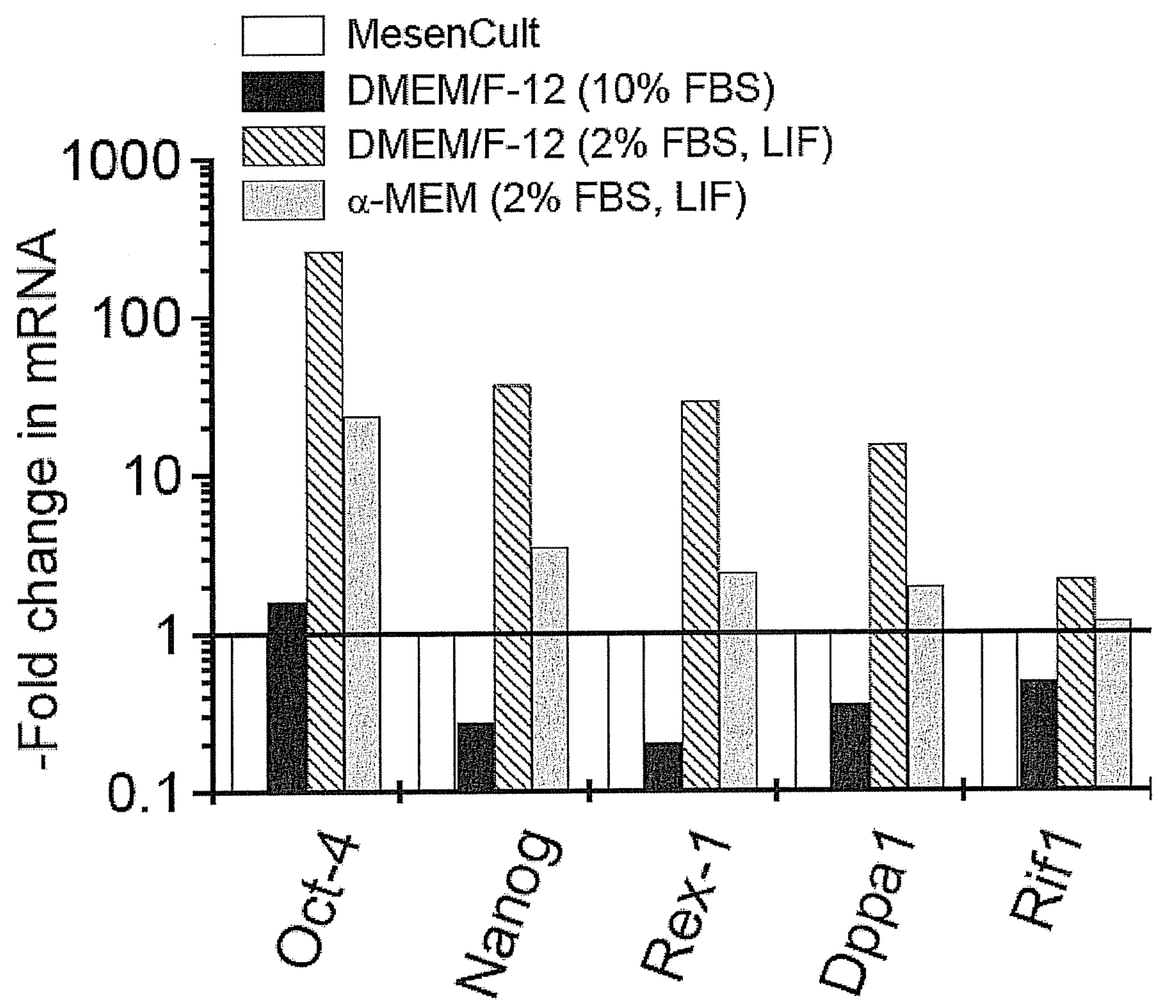

Expression of Markers of Pluripotency are Differentially Influenced by the Expansion Culture Medium Unfractionated MSCs were isolated and expanded in MESENCULT®, DMEM/F-12+10% FBS, DMEM/F-12+2% FBS+LIF, and α-MEM+2% FBS+LIF. Approximately 100,000 cells were collected from each group during passage and mRNA expression levels of various markers of pluripotency (Oct-4, Nanog, Rex-1, Dppa1, and Rif1) were examined by quantitative real-time reverse transcription-polymerase chain reaction (RT-PCR). Three particular observations were made: (i) DMEM/F-12 with low (2%) serum and LIF was the most efficacious in preserving or enhancing the expression of these genes from passage 1 (see FIG. 10A) to passage 2 (see FIG. 10B); (ii) culture medium with high serum, which is most commonly used for MSC expansion, markedly reduced mRNA expression of these genes; and (iii) the expression levels of these different markers, all of which are associated with cellular pluripotency, were differentially affected by the same medium. For example, the changes in expression of Nanog and Dppa1 from passage 1 to passage 2 were different in the same medium (e.g., DMEM/F-12 with 2% FBS and LIF.

These data strongly suggested that optimization of expansion medium can be crucial for expansion of MSCs with respect to the preservation of pluripotency. Also, based on these observations, the use low serum (2% FBS) with serum replacement supplements appeared to be advantageous for expansion of the cells of the presently disclosed subject matter.

Example 11

Figure 11:
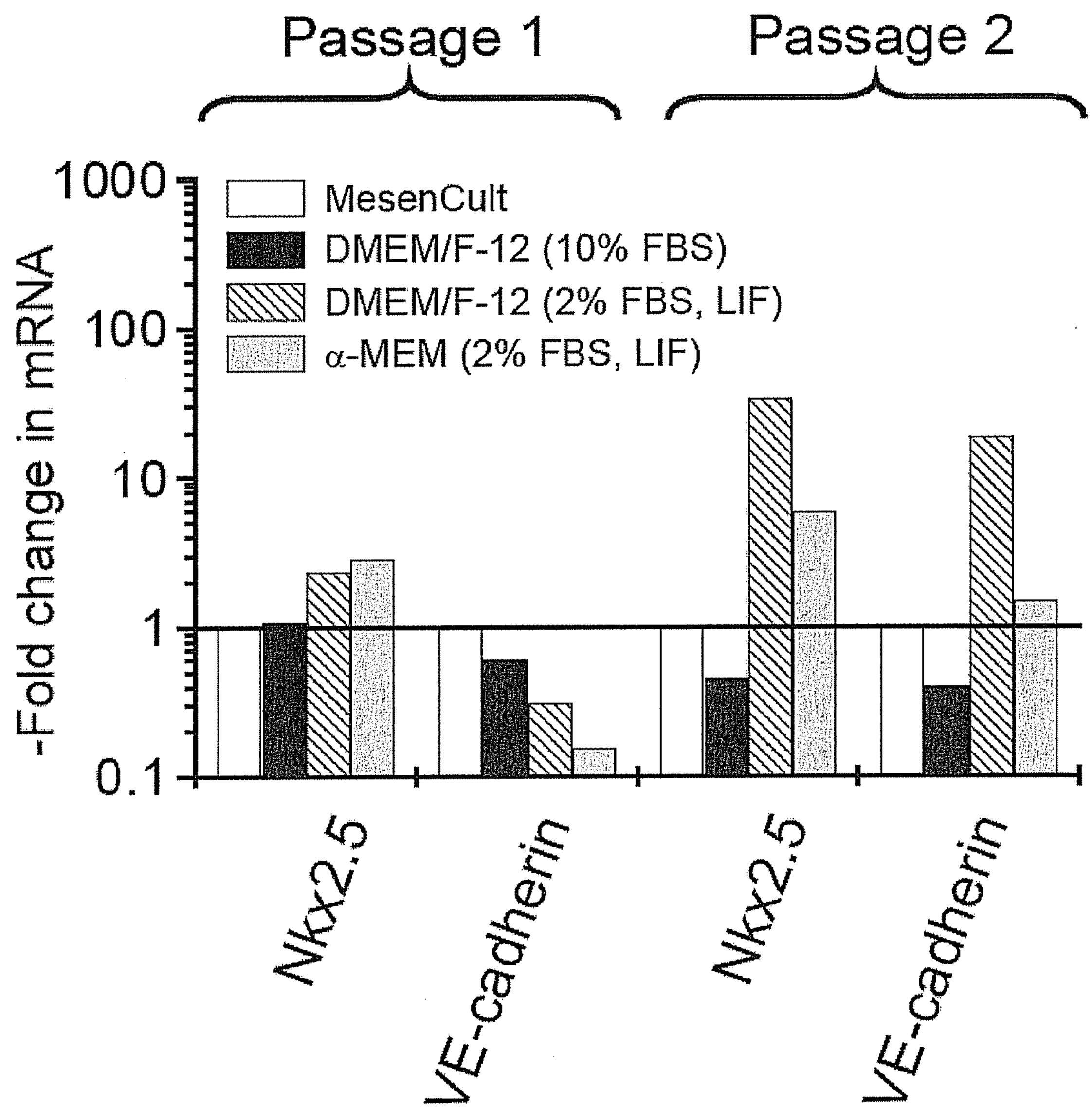
FIG. 11 is a bar graph showing changes in mRNA expression of markers indicative of endothelial and cardiomyogenic lineage commitment during expansion in different media at passages 1 and 2. Fold change was calculated compared with mRNA expression in MESENCULT® culture medium.

Expression Levels of Markers Indicative of Endothelial and Cardiomyogenic Lineage Commitment are Differentially Influenced by the Expansion Culture Medium Unfractionated MSCs were expanded in four different media as in EXAMPLE 10. Approximately 100,000 cells were collected from each group during passage and mRNA expression levels of VE-cadherin (endothelial lineage) and Nkx2.5 (cardiomyogenic lineage) were examined by quantitative real-time RT-PCR. DMEM/F-12 with low serum and LIF was most efficacious in preserving or enhancing the expression of these genes from passage 1 to passage 2 (see FIG. 11), indicating that careful selection of medium might preserve the expression of markers indicative of endothelial and cardiomyogenic lineage commitment in MSCs during expansion.

Example 12

Cardiac Differentiation Potential of Various Subpopulations of Bone Marrow-Derived Adherent Stem Cells Bone marrow mesenchymal stem cells (BMMSCs) are typically isolated as adherent cells; the importance of antigen expression on cardiomyogenic potential of (BMMSCs) remains unclear. Although BMMSCs differentiate into a cardiomyocytic phenotype following 5-azacytidine treatment, the effect of non-toxic growth factors on differentiation induction remains unknown.

The cardiomyogenic potential of two subpopulations of BMMSCs in medium containing growth factors crucial for cardiac development was investigated. $Sca^{-}1^{+}/CD45^{-}/c\text{-}kit^{-}/Thy1^{+}/CD105^{+}$ (BMMSC+) and $Sca\text{-}1^{+}/CD45^{-}/c\text{-}kit^{-}/Thy1^{+}/CD105^{-}$ (BMMSC−) MSCs were obtained from the adherent fraction of BM from C57BL/6 mice using two-step FACS isolation. Cells were differentiated in DMEM with FBS, IGF-1, Dynorphin B, TGFβ-1 and FGF-2. After 30 days of culture, the expression of cardiac-specific transcription factors (TFs) and intracellular antigens (IAs) was quantitatively evaluated by confocal microscopy. BMMSC− cells exhibited greater cardiac differentiation potential compared with BMMSC+ and unfractionated BMMSC populations (29.1±1.7% vs. 15.7±1.6% vs. 15.8±0.9% of cells positive for cardiac markers; see FIG. 15B). BMMSC− cells also exhibited greater angiogenic potential assessed by tube formation after 6 hours of culture in MATRIGEL™ (see FIG. 15C) when compared with BMMSC+ and unfractionated BMMSC populations (364±11.4 vs. 268±14.4 vs. 293.7±33.6 of endotubules per field; see FIG. 15D).

These results indicated that selected nontoxic growth factors could effectively induce cardiac differentiation of BMMSCs and that BMMSCs lacking CD105 expression have greater proclivity to cardiac and endothelial differentiation.

Example 13

Examination of mRNA Expression for Markers of Pluripotency and Markers of Endothelial and Cardiomyogenic Lineage Commitment by Real-time RT-PCR Total mRNA is extracted from approximately 100,000 MSCs from each group and reverse-transcribed. Quantitative assessment of mRNA expression of the genes of interest (including, but not limited to Oct-4, Nanog, Rex-1, Dppa1, Rif1, Nkx2.5, GATA-4, Myl2, Myh6, Isl1, CD31, vWF, Flk-1, VE-cadherin) and β2-microglobulin is performed by real-time RT-PCR using an ABI PRISM® 7000 Sequence Detection System (Applied Biosystems, Foster City, Calif., United States of America) according to standard methods (see e.g., Zuba-Surma et al., 2006). Primers have been designed with the PRIMER EXPRESS® software (Applied Biosystems) and verified.

Example 14

Isolation of Adult Mouse Cardiomyocytes

Ventricular myocytes are isolated from 8-10 week old wild type C57/BL6 mice according to published methods (see e.g., Zhou et al. Shinmura et al. 2005). Briefly, mice are deeply anesthetized with pentobarbital, the heart rapidly excised, aorta cannulated with a 23-gauge needle, the isolated heart mounted and perfused with Ca $2^{+}$-free Tyrode buffer (4 minutes), and then with Tyrode buffer containing 25 μM $Ca^{2+}$, 75 U/ml collagenase I, 75 U/ml collagenase II (Worthington Biochemical Corp., Lakewood, N.J., United States of America), and 1% albumin. The perfusion temperature is maintained at 37° C., and all buffers continuously bubbled with 95% $O_2$ and 5% $CO_2$. After 12-15 minutes, the heart is rinsed with Tyrode buffer (200 μM $Ca^{2+}$, no collagenase), the LV cut into small pieces, and digested (shaking bath, 37° C., 20 minutes). The dispersed cells are filtered through a nylon mesh. The $Ca^{2+}$ concentration is gradually increased to 1.0 mM by addition of medium 199 without FBS.

Following the assessment of viability, cardiomyocytes are plated on the insert (0.4-μm pore, BD BIOCOAT™, Catalogue #354442; BD Biosciences) and placed above MSCs during co-culture. Since viable adult mouse cardiomyocytes cannot be maintained effectively in culture beyond 72 hours, fresh myocytes are isolated at 48-72-hour intervals for the duration of co-culture experiments.

Example 15

Myocardial Infarction and Preparation of Myocardial Extract

Wild type male mice (C57/BL6, body wt. 20-25 g, age 10-12 weeks) are used. The experimental preparation has been described in detail (see Appendix, Section F.I; see also Guo et al., 1998; Dawn et al. 2004a; Dawn et al., 2004b; Dawn et al. 2006). Mice are anesthetized, intubated, and ventilated. Using a sterile technique, the chest is opened, an 8-0 nylon suture passed under the left anterior descending coronary artery, and a nontraumatic balloon occluder applied. Coronary occlusion is induced by inflating the balloon occluder. After 30 minutes, the balloon is deflated and reperfusion verified. The chest is closed in layers, mice removed from the ventilator, kept warm, given fluids, and allowed 100% oxygen via nasal cone (see Guo et al. 1998; Dawn et al. 2004a; Dawn et al., 2004b; Dawn et al., 2006). Twenty-eight days later, mice are euthanized, the heart excised, and the infarct borderzone dissected out and snap-frozen in liquid nitrogen. This time-point was selected because at 28 days after MI in rodents, the expression of pro-inflammatory and cytotoxic molecules is considerably less and the microenvironment simulates that of postinfarct LV (see Lu et al., 2004; Nian et al., 2004; Ono et al., 1998). Myocardial extract is prepared according to previously published methods (see Pierce et al., 1985). Myocardial tissue sample is homogenized in cold (4° C.) cell culture medium (no serum). Following centrifugation (18,000 g for 15 minutes), the supernatant is collected, the pellet resuspended in medium, homogenized in a glass homogenizer, and centrifuged. This process is repeated three times. The supernatants are pooled and filtered. This procedure has been shown to yield a total protein concentration of 8-12 mg/ml. This extract is used fresh or snap-frozen in liquid nitrogen and stored at −80° C.

Example 16

Western Immunoblotting for Protein Expression

When protein expression is abundant, the expression levels of markers of endothelial and cardiomyogenic lineage commitment are assessed by standard SDS-PAGE Western immmunoblotting (see Dawn et al. 1999 Dawn et al. 2004a; Dawn et al. 2004b). Total protein is isolated from an aliquot of cells using standard methods and 60-100 μg of total protein is used per sample. The specific signals are quantitated and normalized with the β-actin loading control.

Example 17

Figure 13:
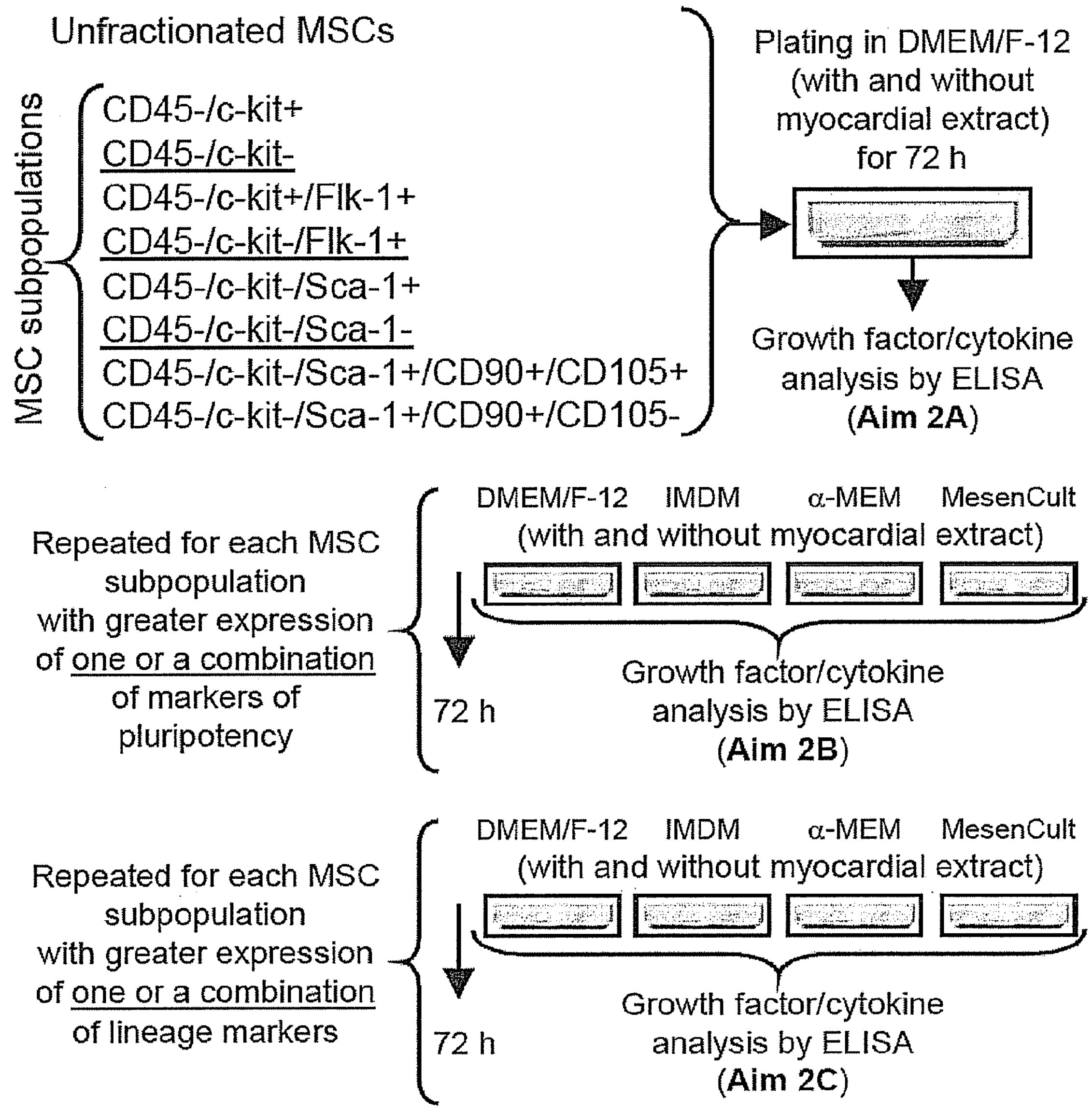
FIG. 13 is a map of an exemplary protocol for measuring secreted growth factors/cytokines multiplex and sandwich ELISA as per EXAMPLE 17.
Figure 14:
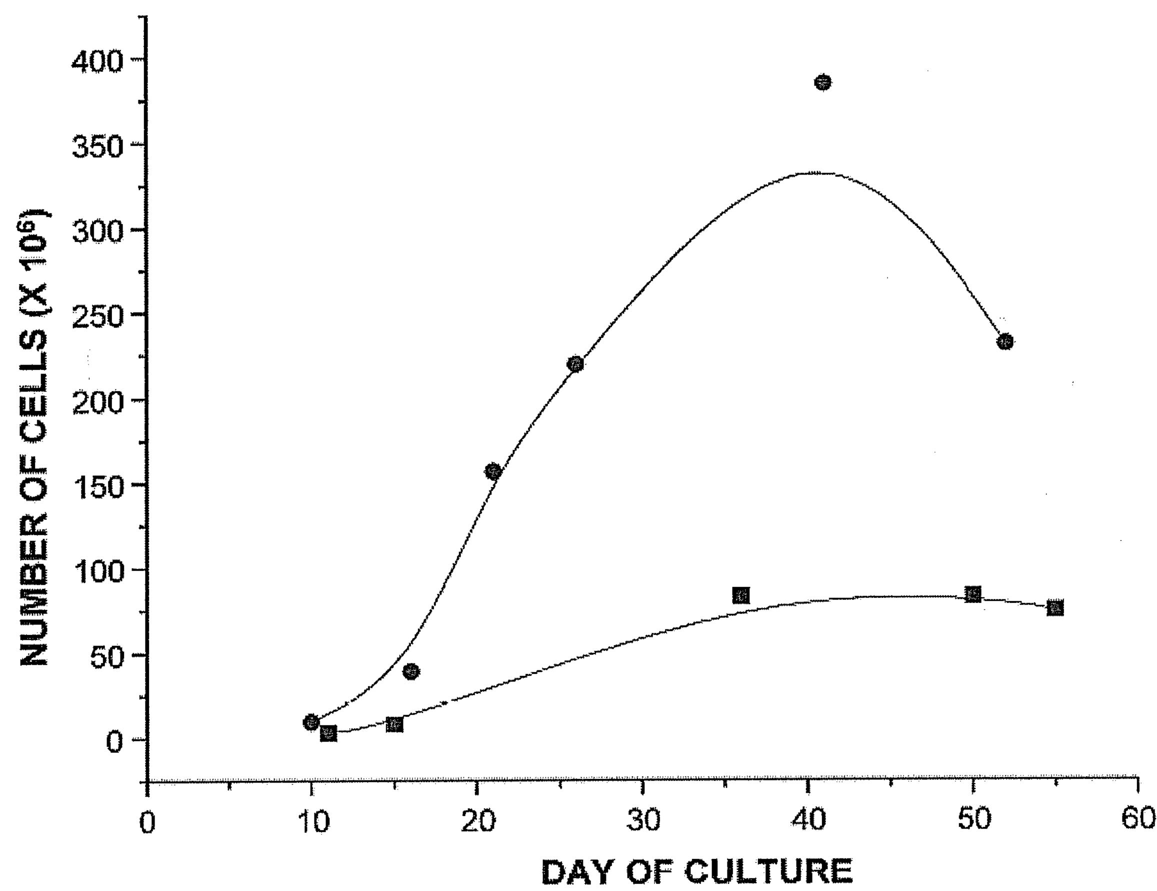
FIG. 14 is a plot showing the impact of different media on the rate of proliferation of unfractionated adherent stem cells in culture over several weeks. ■: DMEM+10% FBS. ●: MESENCULT® culture medium.

Measurement of Secreted Growth Factors/Cytokines by Multiplex and Sandwich ELISA Unfractionated MSCs and MSC subpopulations are plated on uncoated plates in different primary media (with and without myocardial extract) per experimental protocols (see FIG. 13). Culture supernatants are collected after 72 hours. Multiplex ELISA is performed per manufacturer's protocol using a Luminex 100 system and a customized multiplex ELISA kit (LINCOPLEX™, LINCO Research, Inc., St. Charles, Mo., United States of America) with anti-mouse antibodies against MCP-1, G-CSF, GM-CSF, IL-6, IL-13, TNF-α, IL-1α, and IFN-γ immobilized on microspheres. Sandwich ELISA (anti-mouse VEGF, SCF, SDF-1, TGF-β1, MMP-2, MMP-9, TIMP-1, and anti-human HGF and TIMP-2; R&D Systems, Inc., Minneapolis, Minn., United States of America) is performed according to manufacturer's protocol. The baseline values of specific growth factors/cytokines in myocardial extract (measured in simultaneously cultured myocardial extract without MSCs) are subtracted from the observed values from cultures with MSCs.

Example 18

Expansion of MSCs in Different Media

Figure 15:
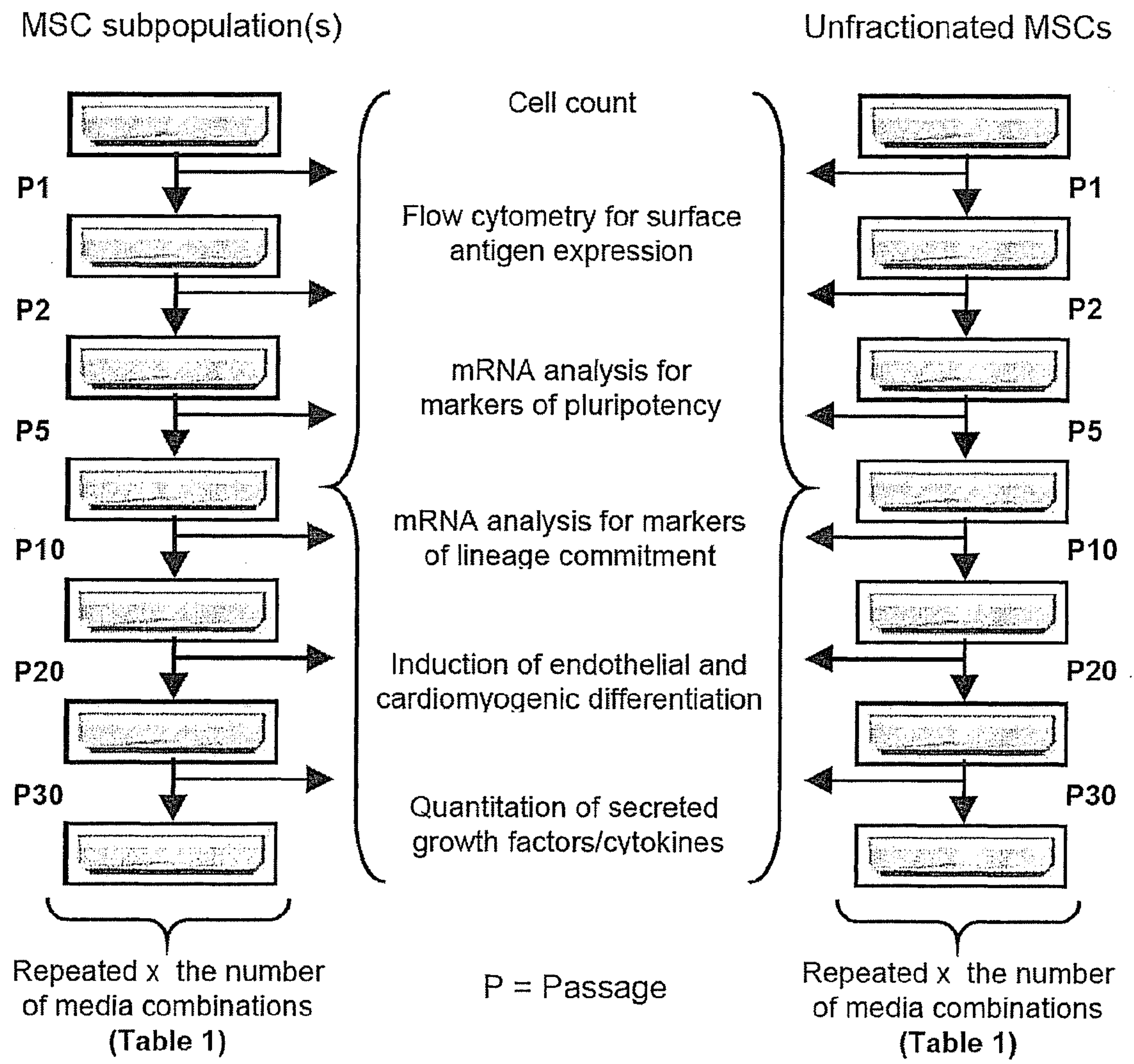
FIG. 15 is a map of an exemplary protocol for expansion of MSCs in different media/growth factor combinations as per EXAMPLE 19.

Following isolation from the whole bone marrow cells, unfractionated adherent stem cells were isolated by adhesion and expanded in culture. Two different media were used: DMEM-F12 with 10% fetal bovine serum and MESENCULT® culture medium. With progressive cellular proliferation, passage was regularly performed when cell density reached approximately 60-70% confluence. On average, cells were passaged at approximately 7-10 day intervals. As shown in FIG. 15, culture in MESENCULT® culture medium resulted in greater proliferation rate compared with DMEM-F12.

Example 19

Expansion of MSCs in Different Media/Growth Factor Combinations

The ability of various media supplemented with different growth factors is tested. A representative scheme for these studies is set forth in FIG. 15. Briefly, unfractionated MSCs and MSC subpopulations are plated in combinations of primary media (DMEM/F-12, IMDM, α-MEM, and MESENCULT®) and factors (LIF, IGF-1, FGF-2, PDGF-B, and Wnt3a; see Table 2). Half of the medium is changed every 3-4 days and cells passaged when confluence reaches approximately 70% (every 7-10 days). Following trypsinization, the total number of cells at each passage is estimated by counting in a hemocytometer using an inverted microscope (Axiovert, Carl Zeiss, Inc.). Cell viability is assessed at each passage.

TABLE 2

Media Combinations for Expansion of MSCs

| | Primary medium | Serum | Growth factors |
|---|---|---|---|
| 1 | DMEM/F-12 | 2% FBS | None |
| 2 | DMEM/F-12 | 2% FBS | LIF |
| 3 | DMEM/F-12 | 2% FBS | LIF, IGF-1 |
| 4 | DMEM/F-12 | 2% FBS | LIF, IGF-1, FGF-2 |
| 5 | DMEM/F-12 | 2% FBS | LIF, IGF-1, PDGF-B |
| 6 | DMEM/F-12 | 2% FBS | LIF, Wnt3a |
| 7 | IMDM | 2% FBS | None |
| 8 | IMDM | 2% FBS | LIF |
| 9 | IMDM | 2% FBS | LIF, IGF-1 |
| 10 | IMDM | 2% FBS | LIF, IGF-1, FGF-2 |
| 11 | IMDM | 2% FBS | LIF, IGF-1, PDGF-B |
| 12 | IMDM | 2% FBS | LIF, Wnt3a |
| 13 | α-MEM | 2% FBS | None |
| 14 | α-MEM | 2% FBS | LIF |
| 15 | α-MEM | 2% FBS | LIF, IGF-1 |
| 16 | α-MEM | 2% FBS | LIF, IGF-1, FGF-2 |
| 17 | α-MEM | 2% FBS | LIF, IGF-1, PDGF-B |
| 18 | α-MEM | 2% FBS | LIF, Wnt3a |
| 19 | MESENCULT ® | 2% FBS | None |
| 20 | MESENCULT ® | 2% FBS | LIF |
| 21 | MESENCULT ® | 2% FBS | LIF, IGF-1 |
| 22 | MESENCULT ® | 2% FBS | LIF, IGF-1, FGE-2 |
| 23 | MESENCULT ® | 2% FBS | LIF, IGF-1, PDGF-B |
| 24 | MESENCULT ® | 2% FBS | LIF, Wnt3a |

Example 20

Analysis of Surface Antigen Expression During Expansion by Flow Cytometry

During each passage, an aliquot of cells (approximately 500,000 cells) from each plate is stained for expression of various markers as set forth in EXAMPLE 5. Expression levels of CD45 (APC, APC-Cy7, PE-Cy7, or FITC), c-kit (PE, APC, or APC-Cy7), Flk-1-PE, Sca-1 (FITC or PE), CD90-PE, and CD105-APC are assayed and analyzed using a MOFLO™ High-Performance Cell Sorter (Dako) and the Summit software. Additional common MSC antigens, including CD31 (FITC or APC), CD29 (ALEXA FLUOR® 488), CD44 (ALEXA FLUOR® 488) are also used. CD11b-PE is used to exclude hematopoietic cells, including macrophages.

Example 21

Statistical Analysis

The primary end-points of these studies are: (i) the percentage of cells expressing specific surface antigens by flow cytometric analysis; (ii) the fold change in mRNA expression of markers of pluripotency, and endothelial and cardiomyogenic lineage commitment by real-time RT-PCR; (iii) the percentage of cells positive for markers of pluripotency and lineage commitment by immunocytochemistry; (iv) the levels of antigens and growth factors/cytokines detected by ELISA and Western immunoblotting; and (v) the estimated number of cells during passage. These parameters are assessed by a two-way (repeated measures, for the same population, as necessary) ANOVA (see Wallenstein et al., 1980). When the ANOVA shows an overall difference, post hoc contrasts are performed using Tukey's t-tests or Student's t-tests with the Bonferroni correction (see Wallenstein et al., 1980). All experiments are performed in triplicate. If larger sample size appears to be necessary, the experiments are repeated under the same conditions. A P value of <0.05 is considered statistically significant.

Materials and Methods for Example 22

Assessment of Cardiac Function by Echocardiography. Echocardiography is performed using previously published methods (see Dawn et al. 2005). Rats are anesthetized with pentobarbital (50 mg/kg i.p., a dose that produces only a modest reduction in LV EF). Core body temperature (maintained with a heating pad), heart rate, and ECG are monitored continuously. Imaging is performed using a HDI 5000 SonoCT echocardiography machine fitted with a 15-7 MHz linear broad-band transducer (Philips Medical Systems International B.V.; Best, the Netherlands). The parasternal long-axis, parasternal short-axis, and apical four-chamber views are used to obtain two-dimensional (2-D), M-mode, and spectral Doppler images. LV FS, LV EF, and LV FAC are calculated from the parasternal short-axis 2-D and M-mode images according to published methods.

Assessment of Cardiac Function by Invasive Hemodynamic Studies. Hemodynamic studies are ormed using previously published methods (Beltrami et al., 2003). Rats are anesthetized with pentobarbital (50 mg/kg i.p.), intubated, and ventilated. A Millar 2 Fr ultraminiature conductance catheter specially designed for rat hearts is inserted from the right carotid artery into the LV for pressure-volume (PV) measurements using the ARIA-1 conductance system. The inferior vena cava (IVC) is exposed and IVC occlusion (IVCO) is performed with external compression. IVCO produces variably loaded beats for determination of the end-systolic PV relation (ESPVR) and other derived constructs of LV performance. Hemodynamics and PV loops are recorded during steady-state and IVCO at baseline and after autonomic blockade with atropine and hexamethonium, a ganglionic blocker, given to obviate reflex effects on LV function. β-adrenergic sensitivity is then measured to evaluate inotropic reserve. Isoproterenol is given via i.v. bolus administration every 5 minutes at 1, 10, 50, and 100 pg/g with steady-state recordings made 1 minute after each dose. LV systolic function is evaluated by ejection fraction, $dP/dt_{max}$, the ESPVR, stroke work (SW)-end-diastolic volume (EDV) relation, $dP/dt_{max}$-EDV relation, and mechanical efficiency as previously described. LV diastolic function is evaluated by the EDPVR, tau (the time constant of relaxation), and Kc (LV chamber stiffness constant). Catecholamine responsiveness is indexed by the increase in dP/dtmax acutely effected by escalating doses of isoproterenol.

Assessment of Differentiation of Injected Adherent Stem Cell Subpopulations into Cardiomyocytes and Endothelial Cells (Cardiac Regeneration) by Immunohistochemistry. In both control and stem cell-injected rats, cardiomyocytes are identified by immunostaining for cardiac specific antigens (e.g., troponin-T, cardiac-specific myosin, desmin, and connexin 43). Newly-formed cardiomyocytes are identified by immunostaining for Nkx2.5, a transcription factor restricted to the initial phases of myocyte differentiation (Dawn et al., 2005; Dawn et al. 2006). Endothelial cells and smooth muscle cells are identified with anti-factor VIII and anti-α-smooth muscle actin antibodies, respectively (Dawn et al., 2005; Dawn et al., 2006). The differentiation of stem cells is also assessed by adding 5-bromodeoxyuridine (BrdU) in drinking water (for the labeling of nuclei in the S-phase of the cell cycle) for 5 d prior to euthanasia (Dawn et al. 2006). BrdU and Ki67, expressed in cycling cells in G1, S, G2, and early mitosis, are detected by immunofluorescent examination of paraffin-embedded myocardial sections. In stem cell-injected rats, dual immunohistochemistry for EGFP (from donor cells) and cardiac specific antigens (e.g., troponin-T, cardiac myosin, Nkx2.5, desmin, and connexin 43) is used to identify stem cell-derived cardiac cells (endothelial cells and cardiomyocytes; Dawn et al., 2005; Dawn et al. 2006). In adherent stem cell-injected rats, dual immunohistochemistry for EGFP (from donor cells) and cardiac-specific (e.g., troponin-T, cardiac myosin, Nkx2.5, desmin, and connexin 43) and endothelial-specific (e.g., CD31, vWF) is used to identify stem cell-derived cardiac cells (Dawn et al., 2005; Dawn et al., 2006).

Myocardial Infarction Protocol. A rat model of myocardial infarction is be used for these studies (Dawn et al., 2005). Experience accumulated over the past six years has demonstrated that this model is not only reliable but also physiologically relevant. The 90-minute occlusion/reperfusion protocol yields reproducible infarcts with small variability. In addition, fundamental physiologic variables that impact on infarct size (arterial blood pressure, heart rate, arterial blood gases, and body temperature) are carefully measured and maintained within normal limits. Athymic nude rats (age, 2-3 months; weight, 150±20 g; Harlan Sprague-Dawley, Indianapolis, Ind., United States of America) are anesthetized with ketamine (37 mg/kg) and xylazine (5 mg/kg) and ventilated with a rodent respirator (Harvard Apparatus; Holliston, Mass., United States of America). Anesthesia is maintained with isoflurane inhalation and body temperature is maintained at 37° C. with a heating pad. After administration of antibiotics, the chest is opened through a midline sternotomy with the aid of a dissecting microscope (Fisher Scientific, Pittsburgh, Pa., United States of America) and a microcoagulator (ASSI Polar-Mate Isolator, San Diego, Calif., United States of America), and a 8-0 nylon suture is passed with a tapered needle underneath the left anterior descending coronary artery 2-3 mm distal to its origin. A nontraumatic balloon occluder is applied on the coronary artery. Coronary occlusion is induced by inflating the balloon occluder. The successful performance of coronary occlusion and reperfusion is verified by visual inspection (i.e., by noting the change of color during occlusion and the return of bright red color after reperfusion) and by observing ST-segment elevation and widening of the QRS complex on the ECG during ischemia and their resolution after reperfusion. All animals undergo a 90-minute occlusion of the left anterior descending coronary artery followed by reperfusion. The chest is then closed and the rat allowed to recover. A small catheter is left in the thorax to evacuate air and fluids. Sham operated rats undergo a 2-hour open-chest state without coronary occlusion. After 35 days of reperfusion, rats are euthanized and the hearts processed for histologic and immunohistochemical analyses.

Transplantation of Adherent Stem Cell Subpopulations. Forty-eight hours or 7 days after MI, rats are re-anesthetized and ventilated and the chest reopened via aseptic technique. Vehicle (50 μl), unfractionated adherent stem cells, or Sca-$1^+$/$CD45^-$/c-$kit^-$/$Thy1^+$/$CD105^-$ stem cell subpopulation ($5\times10^6$ cells in 50 μl) are injected intramyocardially using a 30-gauge needle. A total of five injections are made in the periinfarct region in a circular pattern, at the border between infarcted and noninfarcted myocardium. Sham-operated animals receive similar injections of vehicle or cells. The chest is closed in layers and the rats allowed to recover.

Immunohistochemistry for the Detection of EGFP, Troponin-T, Cardiac Myosin, Connexin 43, Desmin, Nkx2.5, Factor VIII, α-Smooth Muscle Actin. Serial 6-μm sections are cut with a microtome from the formalin-fixed paraffin-embedded heart samples. The primary antibodies (anti-EGFP, troponin-T, cardiac myosin, Nkx2.5, desmin, connexin 43, factor VIII, α-smooth muscle actin) are diluted 1:100 and incubated for 2 hours at room temperature. The primary antibody is detected using fluorochrome-conjugated secondary antibodies.

Morphometric Analysis of Cardiac Structure. Additional morphometric analysis is performed to quantitate cardiac repair as described in (Dawn et al. 2005; Dawn et al. 2006). After measuring the major longitudinal intracavitary axis, the left ventricle (LV) is sectioned serially into five rings perpendicular to the longitudinal axis of the heart, fixed in formalin, processed, and embedded in paraffin. Infarct size is determined from Masson's trichrome-stained serial sections of LV myocardium. From these sections, the thicknesses of the free wall, infarcted region, and septum as well as the transverse LV chamber diameter are determined by an image analyzer. The minimal and maximal luminal diameters at mid-region are used with the longitudinal axis to compute LV chamber volume. Measurements of wall thickness, chamber radius, and LVEDP from hemodynamic studies are used to calculate diastolic wall stress at each site examined. All anatomical parameters are corrected according to a uniform sarcomere length, 2.1 μm.

Statistical analysis. Data are reported as means±SEM. Morphometric, histological, echocardiographic, and hemodynamic data are analyzed with unpaired or paired Student's t-tests, as appropriate. Comparisons involving multiple groups are performed by one- or two-way (time and group) ANOVA as appropriate followed by Student's t-tests with the Bonferroni correction.

Example 22

In vivo Cardiac Repair

Whether transplantation of Sca-$1^+$/$CD45^-$/c-$kit^-$/$Thy1^+$/$CD105^-$ adherent stem cells results in superior cardiac repair by virtue of their inherent propensity to undergo differentiation into cardiac lineages is tested. Studies of cardiac repair in vivo using a well established rat model of myocardial infarction are employed. A clinically-applicable form of stem cell therapy (intramyocardial injection) is employed in a clinically-relevant model of reperfused myocardial infarction (MI). To critically assess the differentiation potential of adult bone-marrow adherent cell subpopulations and consequent infarct repair in vivo, an approach that requires quantitative assessment of cardiac function, anatomy, and cellular differentiation is adopted.

Murine adherent stem cells harvested from the bone marrow of male EGFP transgenic mice are transplanted into the infarct borderzone in infarcted immunocompromised female athymic nude rats. Four days after a baseline echocardiography study, rats undergo a 90-minute coronary occlusion followed by reperfusion as described in Dawn et al., 2005. Culture-expanded unfractionated cells or antigenically-defined adherent stem cell subpopulations ($2\times10^6$ cells in 50 μl) are injected intramyocardially after 4 hours or 7 days of reperfusion as described in Dawn et al. 2008. Serial echocardiography is performed at 48 hours after cell transplantation and again after 35 days see Dawn et al. 2005). Stem cell-injected sham-operated rats and vehicle-injected infarcted rats serve as controls.

Following an invasive hemodynamic study, rats will be sacrificed after 35 days. The hearts are perfusion fixed for infarct size assessment and histologic analysis of cardiac anatomy and infarct repair (see Dawn et al. 2005; Dawn et al., 2008). Quantitative assessment of new cardiomyocyte and vessel formation from EGFP-labeled stem cells is performed (see Dawn et al. 2005; Dawn et al. 2006).

Cardiomyocyte cell cycle activity (BrdU incorporation and Ki67 expression; see Dawn et al. 2005; Dawn et al., 2006) are assessed quantitatively. Additional morphometric (structural) analysis includes measurements of wall thickness at various regions of left ventricle (infarct wall, septum, posterior wall), left ventricular chamber diameter, and cardiomyocyte cross-sectional area (see Dawn et al., 2005; Dawn et al. 2006). Apoptosis in native cardiomyocytes is quantitatively assessed in the infarct area, borderzone, and viable distant myocardium according to standard histological methods (see Kajstura et al. 1996; Yamashita et al., 2001).

Together, these studies directly compare the efficacy of unfractionated adherent stem cells and antigenically-derived subpopulations in cardiac repair after myocardial infarction. By performing extensive histologic analyses, whether the improvement in cardiac structure and function result from differentiation of adherent stem cells into cardiomyocytes and vasculature is determined. Additionally, the in vivo efficacy of differentiation of selected stem cells into endothelial and cardiomyocytic phenotypes is determined.

Example 23

Representative In Vivo Trial

Subpopulations of bone marrow-derived adherent stem cells derived from autologous donors (referred to herein as Autologous Adherent Stem Cell Subpopulations; ASCSes) harvested from bone marrow, cultured and propagated ex vivo, are employed to regenerate infarcted myocardium in patients with acute myocardial infarction (1-3 weeks after acute MI) and ischemic cardiomyopathy (EF <40%) due to prior myocardial infarction.

Number of patients to be enrolled. In a randomized double-blind phase I clinical trial, a total of 80 patients are enrolled in 4 groups: twenty patients with acute myocardial infarction, 20 patients with ischemic cardiomyopathy, 20 control patients with acute MI (standard therapy without cell injection), and 20 control patients with ischemic cardiomyopathy (standard therapy without cell injection).

Dose and route of injection. A total of 20 million ASCSes are injected via the intracoronary route in the infarct-related artery (see Strauer et al. 2005; Lunde et al., 2006; Schachinger et al., 2006). An appropriately sized angioplasty balloon catheter is advanced into the coronary artery over-a-wire. The guidewire is then removed, and the balloon catheter is inflated 4-7 times, for 3 minutes each time at low pressures with 3 minutes of intervening reflow, while ASCSes are infused distal to the occluding balloon through the central port of the catheter. This procedure increases the time available for transmigration of cells through the endothelial lining. Balloon inflations are performed at low pressures (≦3 atmospheres) within a coronary artery so as not to induce any clinically significant endothelial injury/disruption. The control patients receive vehicle injection during the same procedure. The catheter is withdrawn at the end of procedure. Optionally, other delivery methods, including intramyocardial injection in patients undergoing CABG (Hendrikx et al., 2006) are also examined.

Comprehensive assessment of cardiac repair and impact of ASCS transplantation on cardiac structure, function, perfusion, and patient symptoms. All patients undergo a baseline (prior to cell injection) contrast enhanced MRI examination to accurately document cardiac anatomy, infarct volume, myocardial wall motion, and ejection fraction (see Britten et al. 2003; Lunde et al., 2006). Similar assessment of LV function and anatomy are carried out by echocardiographic examinations (see Lunde et al. 2006; Schachinger et al., 2006) at the same time-points. A nuclear perfusion imaging study is performed prior to cell injection to assess myocardial perfusion (Strauer et al., 2002). Baseline clinical variables, including patient symptoms, are documented. Relevant laboratory tests (serum electrolytes, biomarkers of ischemia and heart failure, etc.) are performed before cell injection.

Following ASCS transplantation, cardiac parameters are followed-up with serial MRI imaging at 1, 3, 6, 12, and 24 months after cell injection. Nuclear perfusion imaging are performed at 6, 12, and 24 months. Clinical variables and patient symptoms (see Lunde et al. 2006; Schachinger et al. 2006) are followed-up during serial office visits at 1, 3, 6, 9, 12, months and at 3 month intervals thereafter until 24 months. Relevant laboratory tests are performed during office visits.

REFERENCES

The references listed below as well as all references cited in the specification, including patents, patent applications, journal articles, and all database entries (e.g., GENBANK® Accession Nos., including any annotations presented in the GENBANK® database that are associated with the disclosed sequences), are incorporated herein by reference to the extent that they supplement, explain, provide a background for, or teach methodology, techniques, and/or compositions employed herein.

Abbott et al. Circulation. 2004; 110:3300-3305.

Askari et al. *Lancet.* 2003; 362:697-703.

Balsam et al. *Nature.* 2004; 428:668-673.

Beltrami et al. *Cell.* 2003; 114:763-76.

Berry et al. *Am J Physiol Heart Circ Physiol.* 2006; 290: H2196-2203.

Braunwald & Bristow *Circulation.* 2000; 102:IV14-23.

Britten et al. *Circulation.* 2003; 108:2212-8.

Chien *Nature.* 2004; 428:607-608.

Creemers et al. *Circ Res.* 2001; 89:201-210.

Dai et al. *Circulation.* 2005; 112:214-223.

Dawn et al. *Circ Res.* 1999; 85:1154-1163.

Dawn et al. *Cardiovasc Res.* 2004a; 64:61-71.

Dawn et al. *J Mol Cell Cardiol.* 2004b; 37:51-61.

Dawn et al. *Proc Natl Acad Sci USA.* 2005; 102:3766-3771.

Dawn et al. *Circ Res.* 2006; 98:1098-1105.

Dawn et al. *Stem Cells.* 2008; 26:1646-55.

Deans & Moseley *Exp Hematol.* 2000; 28:875-884.

Ducharme et al. *J Clin Invest* 2000; 106:55-62.

Freyman et al. *Eur Heart J.* 2006; 27:1114-1122.

Friedenstein et al. *Transplantation.* 1968; 6:230-247.

Friedenstein et al. *Cell Tissue Kinet.* 1970; 3:393-403.

Friedenstein et al. *Exp Hematol.* 1976; 4:267-274.

GENBANK® Accession Nos. NM_000118; NM_000222; NM_001003341; NM_001009318; NM_001025109; NM_001093772; NM_001107202; NM_001109887; NM_001109889; NM_001109890; NM_001111059; NM_001111316; NM_001773; NM_002838;

NM_006288; NM_007932; NM_009382; NM_010738; NM_011210; NM_021099; NM_080921; NM_080922; NM_133654; NM_138507; NM_174009; NM_214086; NP_000109; NP_000213; NP_001003341; NP_001009318; NP_001020280; NP_001087241; NP_001100672; NP_001103357; NP_001103359; NP_001103360; NP_001104529; NP_001104786; NP_001764; NP_002829; NP_006279; NP_031958; NP_033408; NP_034868; NP_035340; NP_066922; NP_563578; NP_563579; NP_598415; NP_612516; NP_776434; NP_999251; XM_547374; XM_599431; XP_547374; XP_599431.

Gnecchi et al. *Nat Med.* 2005; 11:367-368.

Gojo et al. *Exp Cell Res.* 2003; 288:51-59.

Grauss et al. *Am J Physiol Heart Circ Physiol.* 2007; 293: H2438-47.

Grinnemo et al. *Ann Med.* 2006; 38:144-153.

Guo et al. *Am J Physiol.* 1998; 275:H1375-1387.

Hattan et al. *Cardiovasc Res.* 2005; 65:334-344.

Heart Disease and Stroke Statistics—2006 Update. A Report From the American Heart Association Statistics Committee and Stroke Statistics Subcommittee. *Circulation.* 2006; 113:e85.

Hendrikx et al. *Circulation.* 2006; 114:I101-7.

Irwin et al. *Circulation.* 1999; 99:1492-1498.

Kajstura et al. *Lab Invest.* 1996; 74:86-107.

Kawada et al. *Blood.* 2004; 104:3581-3587.

Kinnaird et al. *Circulation.* 2004a; 109:1543-1549.

Kinnaird et al. *Circ Res.* 2004b; 95:354-363.

Krause et al. *Stem Cells Dev.* 2007; 16:31-7.

Laflamme & Murry *Nat Biotechnol* 2005; 23:845-856.

Lapidot *Ann N Y Acad Sci.* 2001; 938:83-95.

Le Blanc et al. *Curr Opin Immunol.* 2006; 18:586-591.

Leung et al. *Science.* 1989; 246:1306-1309.

Li et al. *Cardiovasc Res.* 2000; 46:214-224.

Lu et al. *Biochem Biophys Res Commun.* 2004; 321:879-885.

Lunde et al. *N Engl J Med.* 2006; 355:1199-209.

Majumdar et al. *J Cell Physiol.* 1998; 176:57-66.

Mangi et al. *Nat Med.* 2003; 9:1195-1201.

McMurray & Pfeffer *Lancet.* 2005; 365:1877-1889.

Minguell et al. *Exp Biol Med* (Maywood). 2001; 226:507-520.

Miyahara et al. *Nat Med.* 2006; 12:459-65.

Murry et al. *Nature.* 2004; 428:664-668.

Nagaya et al. *Circulation.* 2005; 112:1128-1135.

Nian et al. *Circ Res.* 2004; 94:1543-1553.

Nicosia et al. *Am J Pathol.* 1994; 145:1023-1029.

Ono et al. *Circulation.* 1998; 98:149-156.

Oral et al. *Clin Cardiol.* 1995; 18(9 Suppl 4):IV20-27.

Pfeffer et al. *Circ Res.* 1979; 44:503-512.

Pfeffer et al. *Circulation.* 1990; 81:1161-1172.

Phinney et al. *J Cell Biochem.* 1999; 72:570-585.

Pierce et al. *Am J Physiol.* 1985; 249:C248-255.

Pittenger et al. *Circ Res.* 2004; 95:9-20.

Prockop *Science.* 1997; 276:71-74.

Rohde et al. *Circulation.* 1999; 99:3063-3070.

Rosen et al. *Symp Soc Exp Biol.* 1993; 47:227-234.

Schachinger et al. *N Engl J Med.* 2006; 355:1210-21.

Shinmura et al. *Am J Physiol Heart Circ Physiol.* 2005; 288:H2093-2101.

Silva et al. *Stem Cells.* 2003; 21:661-669.

Strauer et al. *Circulation.* 2002; 106:1913-8.

Strauer et al. *J Am Coll Cardiol.* 2005; 46:1651-8.

Tang et al. *J Am Coll Cardiol.* 2005; 46:1339-1350.

Toma et al. *Circulation.* 2002; 105:93-98.

Tomita et al. *Circulation.* 1999; 100(19 Suppl):II247-256.

U.S. Pat. Nos. 5,736,396; 5,750,397.

Vassilopoulos et al. *Curr Opin Genet Dev.* 2003; 13:480-485.

Wallenstein et al. *Circ Res.* 1980; 47:1-9.

Wang et al. *Am J Physiol Heart Circ Physiol.* 2006; 290: H1393-1405.

Wang et al. *Nature.* 2003; 422:897-901.

Yamashita et al. *Circ Res.* 2001; 88:609-14.

Zhang et al. *FASEB J.* 2007; 21:3197-207.

Zhou et al. *Am J Physiol Heart Circ Physiol.* 2000; 279: H429-436.

Zuba-Surma et al. *J Mol Cell Cardiol.* 2006; 41:650-660.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An isolated subpopulation of bone marrow-derived adherent stem cells, wherein the isolated subpopulation of bone marrow-derived adherent stem cells comprises at least about 50% of either $CD34^+/CD45^-/c\text{-}kit^-/Thy1^+/CD105^-$ or $Sca\text{-}1^+/CD45^-/c\text{-}kit^-/Thy1^+/CD105^-$ cells isolated from adherent bone marrow cells.

2. A composition comprising the isolated subpopulation of bone marrow-derived adherent stem cells of claim 1 and a pharmaceutically acceptable carrier.

3. The composition of claim 2, wherein the pharmaceutically acceptable carrier is pharmaceutically acceptable for use in a human.

4. The isolated subpopulation of bone marrow-derived adherent stem cells of claim 1, wherein the $CD34^+/CD45^-/c\text{-}kit^-/Thy1^+/CD105^-$ cells or the $Sca\text{-}1^+/CD45^-/c\text{-}kit^-/Thy1^+/CD105^-$ cells make up at least about 95% of the cells in the isolated subpopulation.

5. The composition of claim 2, wherein the $CD34^+/CD45^-/c\text{-}kit^-/Thy1^+/CD105^-$ cells or the $Sca\text{-}1^+/CD45^-/c\text{-}kit^-/Thy1^+/CD105^-$ cells make up at least about 95% of the cells present in the composition.

* * * * *